(12) United States Patent
Ryu et al.

(10) Patent No.: US 11,697,009 B2
(45) Date of Patent: Jul. 11, 2023

(54) MICRONEEDLE PATCH, MICRO NEEDLE SYSTEM AND METHOD OF FABRICATING THE SAME

(71) Applicant: Industry-Academic Cooperation Foundation, Yonsei University, Seoul (KR)

(72) Inventors: WonHyoung Ryu, Goyang-si (KR); SeungHyun Park, Seoul (KR); JiYong Lee, Seoul (KR); Jae Ho Kim, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 321 days.

(21) Appl. No.: 17/012,566

(22) Filed: Sep. 4, 2020

(65) Prior Publication Data
US 2021/0069482 A1    Mar. 11, 2021

(30) Foreign Application Priority Data

Sep. 6, 2019   (KR) ........................ 10-2019-0110987
Sep. 6, 2019   (KR) ........................ 10-2019-0110992
Sep. 6, 2019   (KR) ........................ 10-2019-0111000

(51) Int. Cl.
*A61M 37/00* (2006.01)
*B33Y 80/00* (2015.01)

(52) U.S. Cl.
CPC ......... *A61M 37/0015* (2013.01); *B33Y 80/00* (2014.12); *A61M 2037/0053* (2013.01); *A61M 2205/02* (2013.01)

(58) Field of Classification Search
CPC ...... A61M 37/0015; A61M 2037/0053; A61M 2205/02; A61M 2037/0023; A61M 2037/0046; B33Y 80/00
See application file for complete search history.

(56) References Cited

U.S. PATENT DOCUMENTS

2005/0271684 A1* 12/2005 Trautman .......... A61M 37/0015
                                                          424/234.1
2008/0125743 A1*  5/2008 Yuzhakov ......... A61M 37/0015
                                                            604/506

OTHER PUBLICATIONS

Carneiro, V.H., Meireles, J., and Puga, H., "Auxetic Mateirals–A Review", (2013), Materials Science-Poland, 31(4), pp. 561-571 (Year: 2013).*

* cited by examiner

*Primary Examiner* — Amber R Stiles
(74) *Attorney, Agent, or Firm* — Paratus Law Group, PLLC

(57) ABSTRACT

Disclosed are a microneedle patch and a method for fabricating the microneedle patch. The microneedle patch includes a base layer including a mesh structure or auxetic materials having a negative Poisson's ratio, and a microneedle array disposed on the base layer. The method includes forming a base layer including a mesh structure or auxetic materials having a negative Poisson's ratio, and forming a microneedle array on the base layer.

12 Claims, 29 Drawing Sheets

Fig. 1B
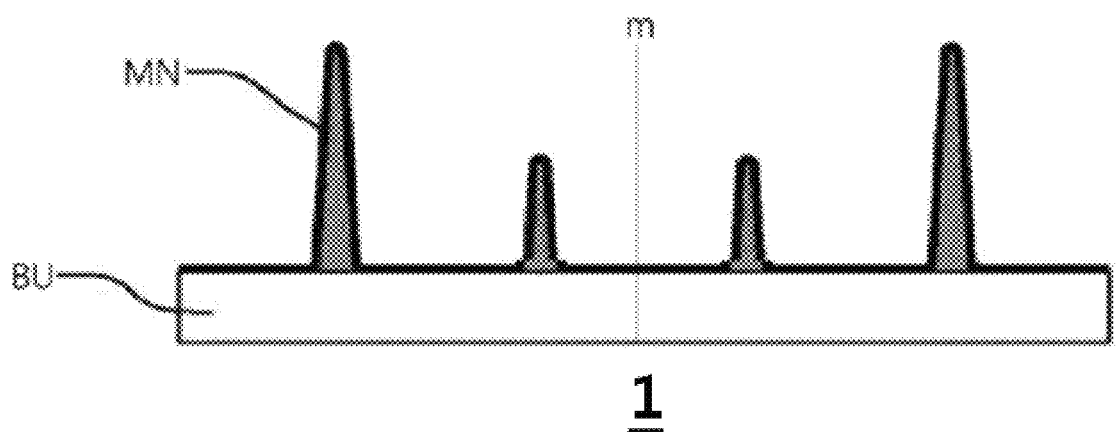
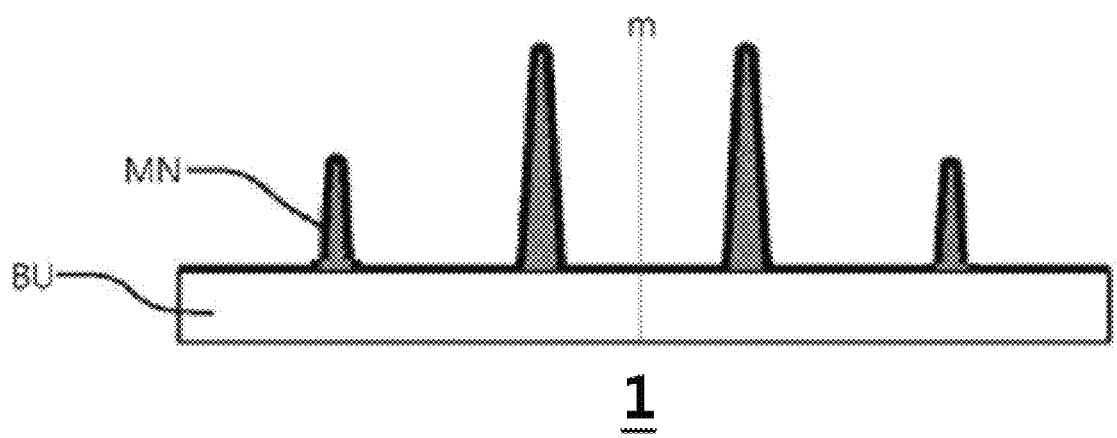

FIG. 5A
FIG. 5B
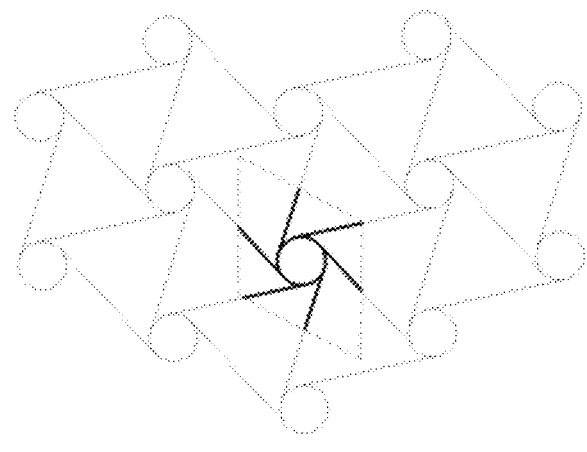
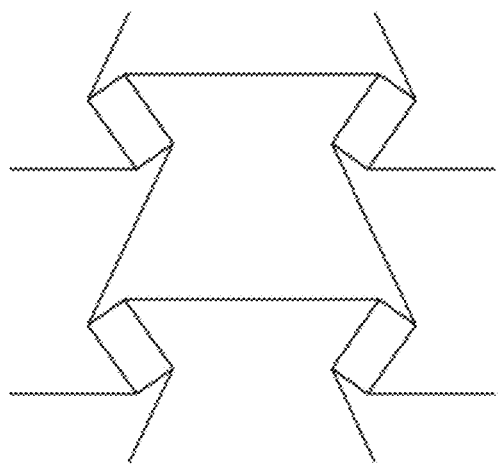

Fig. 14B

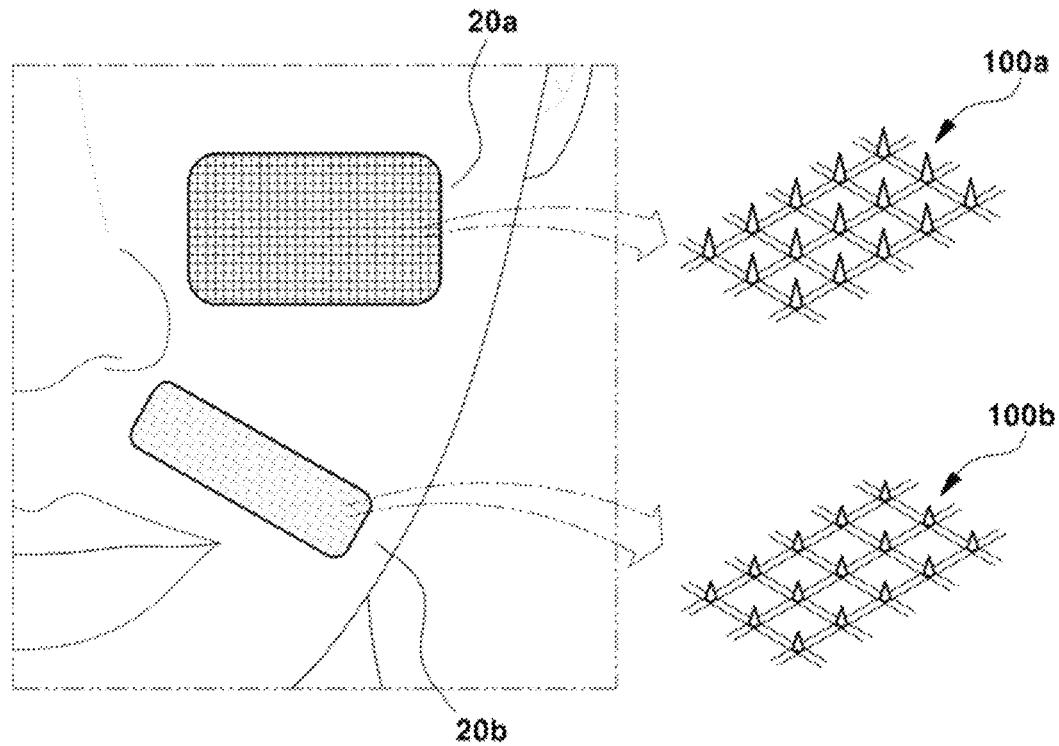

Fig. 15

| PREPARE PLURALITY OF MICRONEEDLES EACH HAVING UPPER END PORTION AND BASE PORTION AND WHICH ARE INDIVIDUALIZED FROM EACH OTHER |
|---|

↓

| FORM BASE LAYER THAT IS FORMED OF WATER-SOLUBLE MATERIAL AND INCLUDES LINEAR PORTIONS THAT PASS BASE PORTIONS OF MICRONEEDLES NEIGHBORING EACH OTHER AND ARE JOINED TO THE BASE PORTIONS OF THE MICRONEEDLES NEIGHBORING EACH OTHER |
|---|

MICRONEEDLE PATCH, MICRO NEEDLE SYSTEM AND METHOD OF FABRICATING THE SAME

CROSS-REFERENCE TO RELATED APPLICATION

This application claims priority to and the benefit of Korean Patent Application No. 10-2019-0110987 filed on Sep. 6, 2019, Korean Patent Application No. 10-2019-0110992 filed on Sep. 6, 2019, and Korean Patent Application No. 10-2019-0111000 filed on Sep. 6, 2019, the disclosure of which is incorporated herein by reference in their entirety.

BACKGROUND

The present invention relates to a microneedle patch, a microneedle system, and a method of fabricating the same. Microneedles are used in delivery of effective materials such as drugs, vitamins, or vaccines into a living body, detection of analytes in the body, or biopsy. Conventionally, the microneedles have been fabricated using materials such as silicon, non-biodegradable polymer, metal, or glass. However, the materials have a problem in that it takes a long time for the effective materials to be diffused in the body at a sufficient amount for the effective materials to take effect.

Also, for the effective materials to be diffused and delivered accurately into the body, the microneedles or a patch on which the microneedles are formed should be appropriately attached. It is preferable that the microneedle or the patch is stably attached to a curved surface of a living body and is not detached from the surface of the living body due to movement of muscles.

However, in the case in which the microneedle patch is attached to a curved skin surface or a surface with frequent skin muscle movement, deformation of the microneedle patch may occur according to a change in the curvature of the skin surface, and the non-uniform deformation may occur in at least a portion or the entire area the microneedle patch. For example, in the case in which tensile deformation occurs in any one portion of the microneedle patch, compressive deformation may occur in another portion of the microneedle patch to compensate for the tensile deformation. In such a case in which deformation of a partial region of the entire region of the microneedle patch causes deformation of another region thereof, since the microneedle patch attached to the skin surface may be partially detached easily, it may be difficult for at least a portion of the microneedle patch to be uniformly adhered to the skin surface.

Also, as described above, for delivery of effective materials, the microneedles should remain in the living body for an appropriate time while being attached to the surface of the living body. However, as described above, a state in which the entire area or a partial area of the microneedle patch is uniformly adhered to the skin surface may be disrupted due to the curvature of the skin surface or skin muscle movement, and a region of the microneedles detached from the skin surface may be separated from the skin. In this case, in the region of the microneedle patch detached from the skin surface, the corresponding microneedles may not deliver a sufficient amount of effective materials, and the effective materials may be delivered to surroundings from a target site instead of being delivered to the target site and unwanted side effects may occur.

As a method for delivery of pharmaceutically, medically, or cosmetically effective materials that are applied to the human body, a method of injecting the effective materials in a liquid form using a hypodermic needle has been widely applied. However, the hypodermic needle, which has a diameter of several millimeters, may stimulate a plurality of pain spots present in the skin and cause pain to a user, so that there is a problem in that using the hypodermic needle requires a high level of skill.

In recent years, in order to overcome the disadvantages of the hypodermic needle, research has been actively performed on a method of percutaneous delivery of the effective materials using a microneedle device of which the diameter and height are only several tens of micrometers or several hundreds of micrometers. The microneedle device forms numerous microchannels that pass through the stratum corneum layer of the skin at one time by using microneedles. A sufficient amount of effective materials may be delivered to the epidermis layer or dermis layer through the microchannels.

For the effective materials to be diffused and delivered accurately into the body, the microneedles or the patch on which the microneedles are formed should be appropriately attached. It is preferable that the microneedle or the patch is stably attached to a curved surface of a living body and is not detached from the surface of the living body due to movement of muscles. As described above, for delivery of effective materials, the microneedles should remain in the living body for an appropriate time while being attached to the surface of the living body. Also, after an appropriate amount of effective materials is released, the microneedles should be removed from the body or biodegraded in the body to prevent unexpected inflammatory responses.

As a method for delivery of pharmaceutically, medically, or cosmetically effective materials into the human body that is applied to the human body, a method of injecting the effective materials in a liquid form using a hypodermic needle has been widely applied. However, the hypodermic needle, which has a diameter of several millimeters, may stimulate a plurality of pain spots present in the skin and cause pain to a user, so that there is a problem in that using the hypodermic needle requires a high level of skill.

In recent years, in order to overcome the disadvantages of the hypodermic needle, research has been actively performed on a method of transdermal delivery of the effective materials using microneedles of which the diameter and height are only several tens of micrometers or several hundreds of micrometers. The microneedles may form numerous microchannels that pass through the stratum corneum layer of the skin, which is the main barrier layer for transdermal drug delivery, at one time, and the microchannels allow a sufficient amount of effective materials to be delivered to the epidermis layer or dermis layer. Then, for example, the effective materials may be absorbed through blood vessels and lymph glands and be brought into the circulation system of the human body.

Microneedles are used in detection of analytes in the body or biopsy as well as in delivery of effective materials such as drugs, vitamins, or vaccines into a living body. Conventionally, the microneedles have been fabricated using materials such as silicon, non-biodegradable polymer, metal, or glass. However, the materials have a problem in that it takes a long time for the effective materials to be diffused in the body at a sufficient amount for the effective materials to take effect.

Also, for the effective materials to be diffused and delivered accurately into the body, the microneedles or a patch on which the microneedles are formed should be appropriately attached to a living body surface such as skin, and a state in which the microneedles are inserted into the living body surface should be stably maintained for an appropriate time. However, generally, a state in which the entire area or a partial area of the microneedle patch is uniformly adhered to the surface of living body may be disrupted due to the surface curvature of living body or movement of living body surface muscles, and a region of the microneedles detached from the living body surface may be separated from the skin. In this case, in the region of the microneedle patch detached from the living body surface, the corresponding microneedles may not deliver a sufficient amount of effective materials, thus being unable to obtain a delivery effect of materials, or the effective materials may be delivered to surroundings from a target site instead of being delivered to the target site and unwanted side effects may occur.

SUMMARY

The present invention is directed to providing a microneedle patch that has an improved adhesiveness even to a curved part of the body and is capable of being stably mounted to allow effective materials to be effectively delivered to the skin.

The present invention is also directed to providing a method of fabricating a microneedle patch that is capable of easily fabricating the microneedle patch in various forms.

The present invention is also directed to providing a microneedle patch that allows microneedles to be stably inserted for effectively delivering effective materials even to a curved part of the body and is capable of stably maintaining a state in which the microneedles are inserted without being detached for an sufficient time for the materials to be released to the part of the body.

The present invention is also directed to providing a microneedle patch that is capable of stably maintaining a state in which microneedles are inserted into a surface of living body to effectively deliver effective materials even when the surface of living body is curved or muscle movement occurs at the surface of living body.

The present invention is also directed to providing a microneedle system that is easy to use and is capable of, using a simple method, maintaining a state in which microneedles are inserted into the skin.

An embodiment of the present invention provides a microneedle patch including a base layer including a mesh structure or auxetic materials having a negative Poisson's ratio, and a microneedle array disposed on the base layer. In an embodiment, the microneedle array may have tensile deformation in a first direction due to a tensile force and tensile deformation in a second direction different from the first direction, and the microneedle array may have compressive deformation in the first direction due to a compressive force and compressive deformation in the second direction different from the first direction. Linear portions connecting a plurality of microneedles included in the microneedle array on the mesh structure or linear portions connecting intersection points of the mesh structure may have a zigzag or serpentine shape. The base layer may include a patterned mesh structure including at least any one of a two-dimensional cut missing rib structure or a two-dimensional re-entrant honeycomb structure. According to an embodiment, the base layer may further include: a plurality of two-dimensional re-entrant honeycomb structures which are spaced apart and stacked, a plurality of two-dimensional cut missing rib structures which are spaced apart and stacked, or mixed structures formed of a combination of the two-dimensional re-entrant honeycomb structures and the two-dimensional cut missing rib structures which are spaced apart and stacked; and interlayer connecting portions disposed between the two-dimensional re-entrant honeycomb structures which are spaced apart and stacked, disposed between the two-dimensional cut missing rib structures which are spaced apart and stacked, or disposed between the mixed structures in which the two-dimensional re-entrant honeycomb structures and the two-dimensional cut missing rib structures are spaced apart and stacked. The microneedle array may include a plurality of microneedles each having an upper end portion and a lower end portion and which are individualized from each other, and the base layer may pass the lower end portions of the microneedles neighboring each other among the plurality of microneedles and be joined to the lower end portions of the microneedles neighboring each other and may be formed of a water-soluble material. The plurality of microneedles may be fixed to the intersection points of the mesh structure. The microneedle patch may further include a plurality of pharmaceutically, medically, or cosmetically effective materials, and the effective materials may be dissolved or dispersed in the plurality of microneedles or be coated on surfaces of the plurality of microneedles. A first group of microneedles among the plurality of microneedles may include a first effective material among the plurality of effective materials, and a second group of microneedles different from the first group may include a second effective material among the plurality of effective materials. The microneedle patch may further include an adhesive layer disposed between the base layer and the plurality of microneedles.

Another embodiment of the present invention provides a method of fabricating a microneedle patch, the method including forming a base layer including a mesh structure or auxetic materials having a negative Poisson's ratio and forming a microneedle array on the base layer. The forming of the base layer or the forming of the microneedle array may be performed by 3D printing, laser cutting, molding, or a combination thereof. The 3D printing may include stereolithography (SLA), digital micromirror device-based projecting printing (DMD-PP), two-photon polymerization (2PP), fused deposition modelling (FDM), inkjet, bioprinting, selective laser melting (SLM), electron beam melting (EBM), or a combination thereof.

A microneedle patch according to an embodiment of the present invention includes a plurality of microneedles each having an upper end portion and a base portion and which are individualized from each other, and a base layer that is formed of a water-soluble material and includes linear portions that pass the base portions of the microneedles neighboring each other among the plurality of microneedles and are joined to the base portions of the microneedles neighboring each other.

In one embodiment, the upper end portions of the plurality of microneedles may each include a sharp end portion, and a maximum diameter of the base portion may be larger than a diameter of the upper end portion. In another embodiment, the plurality of microneedles may be fixed to a region where at least two or more linear portions among the linear portions intersect.

In an embodiment, the base layer may have a mesh structure or a nonwoven structure.

In a embodiment, pharmaceutically, medically, or cosmetically effective materials may be dissolved or dispersed in the plurality of microneedles or be coated on the plurality of microneedles. In another embodiment, the plurality of microneedles may further include, in at least a portion thereof, a plurality of kinds of effective materials, a first group of microneedles among the plurality of microneedles may include a first effective material among the plurality of kinds of effective materials, and a second group of microneedles different from the first group may include a second effective material among the plurality of kinds of effective materials. In still another embodiment, in a case in which the microneedle patch is attached to a target region and moisture is provided to the microneedle patch, the base layer may degrade and subsequently be removed, and the microneedles may remain in a region below the target region.

A method of fabricating a microneedle patch according to an embodiment of the present invention includes preparing a plurality of microneedles each having an upper end portion and a base portion and which are individualized from each other and forming a base layer that is formed of a water-soluble material and includes linear portions that pass the base portions of the microneedles neighboring each other among the plurality of microneedles and are joined to the base portions of the microneedles neighboring each other. In another embodiment, the forming of the base layer may be performed by a printing method in which at least one or more nozzles configured to eject a precursor of the base layer are moved on the plurality of microneedles to form linear portions configured to connect the microneedles neighboring each other. In still another embodiment, the forming of the base layer may be performed by an electrospinning method in which a precursor of the base layer is ejected using an electric field to form linear portions configured to connect the microneedles neighboring each other.

A microneedle patch according to an embodiment of the present invention includes a plurality of microneedles each having an upper end portion and a base portion and which are individualized from each other, and a water-soluble base layer joined to the plurality of microneedles to two-dimensionally arrange the plurality of microneedles, wherein, when the microneedle patch is applied to skin, the plurality of microneedles which are two-dimensionally arranged are individualized as moisture is supplied to the water-soluble base layer and the water-soluble base layer is removed.

In an embodiment, the plurality of microneedles may be formed of a biodegradable material. In another embodiment, the plurality of microneedles may be coated with a keratolytic agent.

In an embodiment, the water-soluble base layer may include a planar structure having a continuous surface, a mesh structure, a through-hole structure, a nonwoven structure, or a porous structure. In another embodiment, the water-soluble base layer may include a material that absorbs heat when it is dissolved.

A microneedle patch according to an embodiment of the present invention includes a plurality of microneedles each having an upper end portion and a base portion and which are individualized from each other, a water-soluble base layer joined to the plurality of microneedles to two-dimensionally arrange the plurality of microneedles, and a moisture supplying member configured to supply moisture to the water-soluble base layer to remove the water-soluble base layer so that the plurality of microneedles which are two-dimensionally arranged are individualized. In another embodiment, the water-soluble base layer may include a plurality of through-pores that act as a movement path along which materials included in the moisture supplying member delivery into the skin.

In an embodiment, the moisture supplying member may be a moisture-containing sheet, a hydrogel sheet, a sheet mask, a moisturizing gel, a moisturizing cream, a toner, an essence, or a combination thereof. In another embodiment, the moisture supplying member may include pharmaceutically, medically, or cosmetically effective materials. In still another embodiment, the microneedles may degrade in the skin and pass through a portion of the skin to form a material exchange channel between the skin and the moisture supply member.

By utilizing a base layer including a mesh structure having a negative Poisson's ratio according to an embodiment of the present invention, it is possible to provide a microneedle patch that has an improved adhesiveness even to a curved part of the body and that is capable of being stably mounted to allow effective materials to be effectively delivered to the skin.

According to an embodiment of the present invention, it is possible to provide a method of fabricating a microneedle that has the advantages described above.

A microneedle patch according to an embodiment of the present invention uses a base layer that absorbs moisture from the outside and reacts with the absorbed moisture and degrades in order to fix microneedles. Thus, the microneedles may be easily separated from the base layer and inserted into the skin, and a case, in which a portion of the base layer remains in the skin and causes discomfort, may be prevented.

Also, since the base layer includes a plurality of linear portions joined to base portions of the microneedles, the microneedle patch has flexibility and may be easily attached to a target site, detachment of an attached portion of the microneedle patch due to muscle movement or movement during the attachment process may be prevented, and the amount of moisture absorbed per unit area of the base layer may be decreased, making it possible to prevent a side effect in which moisture absorption by the base layer causes moisture to be absorbed, rather than provided to, from a part of the body to which the microneedle patch is provided.

A method of fabricating a microneedle patch according to an embodiment of the present invention may easily fabricate a microneedle patch having the advantages described above with high yield.

A microneedle patch according to an embodiment of the present invention uses a water-soluble base layer to fix a plurality of microneedles. Thus, in a case in which moisture is supplied to the water-soluble base layer, the water-soluble base layer may degrade and the microneedles may be easily separated from the water-soluble base layer and inserted into the skin, and when the water-soluble base layer is detached, the microneedles may be prevented from escaping out of the skin along with the water-soluble base layer. In this way, it is possible to achieve a highly efficient medical or cosmetic effect.

A microneedle system according to an embodiment also provides a moisture supply member containing a sufficient amount of moisture to allow degradation of the water-soluble base layer. Thus, without additional effort, a sufficient amount of moisture may be supplied to the water-soluble base layer, and the water-soluble base layer may be removed without any residue. Also, since the microneedles are inserted into the skin and, after being inserted into the skin, degrade and form a material movement path, moisture and/or nutritional components contained in the moisture supplying member may be effectively absorbed into the skin through the material movement path.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1B shows side views of the microneedle patch according to different embodiments of the present invention;

FIGS. 3A, 3B, 4A, 4B, 5A, 5B, 6A, and 6B are views illustrating a mesh structure having a negative Poisson's ratio according to various embodiments of the present invention;

FIG. 14B is a view illustrating how to use the microneedle patch according to an embodiment of the present invention;

FIG. 15 is a flowchart of a method of fabricating a microneedle patch according to an embodiment of the present invention;

DETAILED DESCRIPTION

Figure 1A:
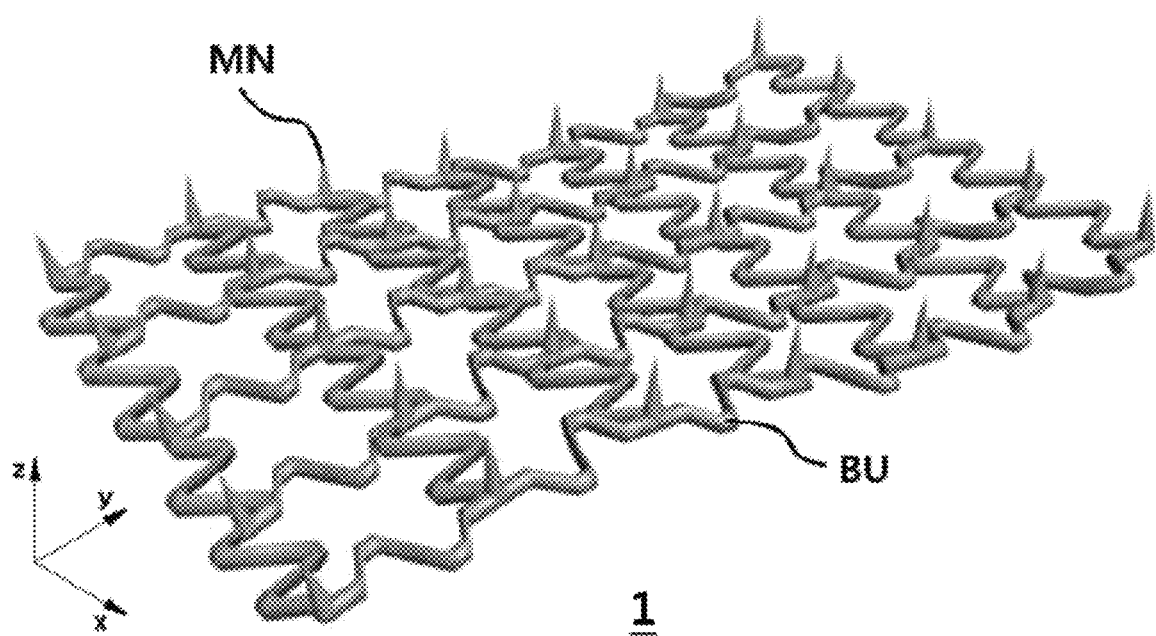
FIG. 1A is a perspective view of a microneedle patch according to an embodiment of the present invention.

Hereinafter, exemplary embodiments of the present invention will be described in detail with reference to the accompanying drawings.

The embodiments of the present invention are provided to more thoroughly describe the present invention to those of ordinary skill in the art. The following embodiments may be modified in various other forms, and the scope of the present invention is not limited to the following embodiments. Rather, the embodiments are provided to make the present disclosure more complete and to fully convey the idea of the present invention to those of ordinary skill in the art.

Also, the thickness or size of each layer in the drawings has been exaggerated for convenience and clarity of description, and like reference numerals refer to like elements in the drawings. As used herein, the term "and/or" includes any one of the associated listed items and all combinations of one or more of the associated listed items.

The terms used herein are used to describe specific embodiments and are not intended to limit the present invention. As used herein, a singular expression may include a plural expression unless the context clearly indicates otherwise. Also, "comprise" and/or "comprising," when used herein, designate the presence of shapes, numbers, steps, operations, members, elements, and/or groups thereof mentioned herein and do not preclude the presence or the possibility of adding one or more shapes, numbers, steps, operations, members, elements, and/or groups other than those mentioned.

Terms such as first and second are used herein to describe various members, components, regions, and/or portions, but it is apparent that the members, components, regions, and/or portions are not limited by the terms. The terms are only used to distinguish one member, component, region, or portion from another region or portion. Therefore, a first member/component/region/portion may also be referred to as a second member/component/region/portion without departing from the scope of the present invention.

Hereinafter, embodiments of the present invention will be described with reference to the drawings that schematically illustrate ideal embodiments of the present invention. In the drawings, for example, sizes and shapes of members may have been exaggerated for convenience and clarity of description, and modifications of the illustrated shapes during actual implementation may be expected. Therefore, the embodiments of the present invention should not be interpreted as being limited to specific shapes of members or regions illustrated in the drawings.

First Embodiment

Figure 2A:
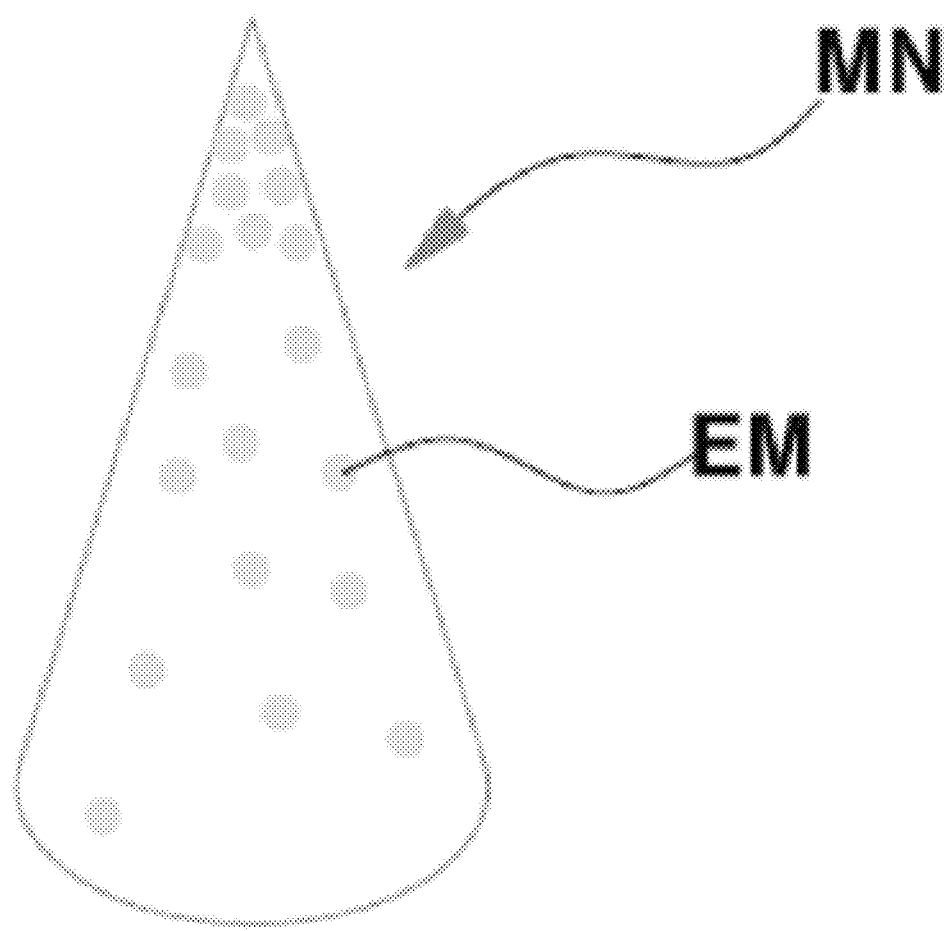
FIGS. 2A and 2B are views illustrating one microneedle among a plurality of microneedles of the microneedle patch according to an embodiment of the present invention.
Figure 2B:
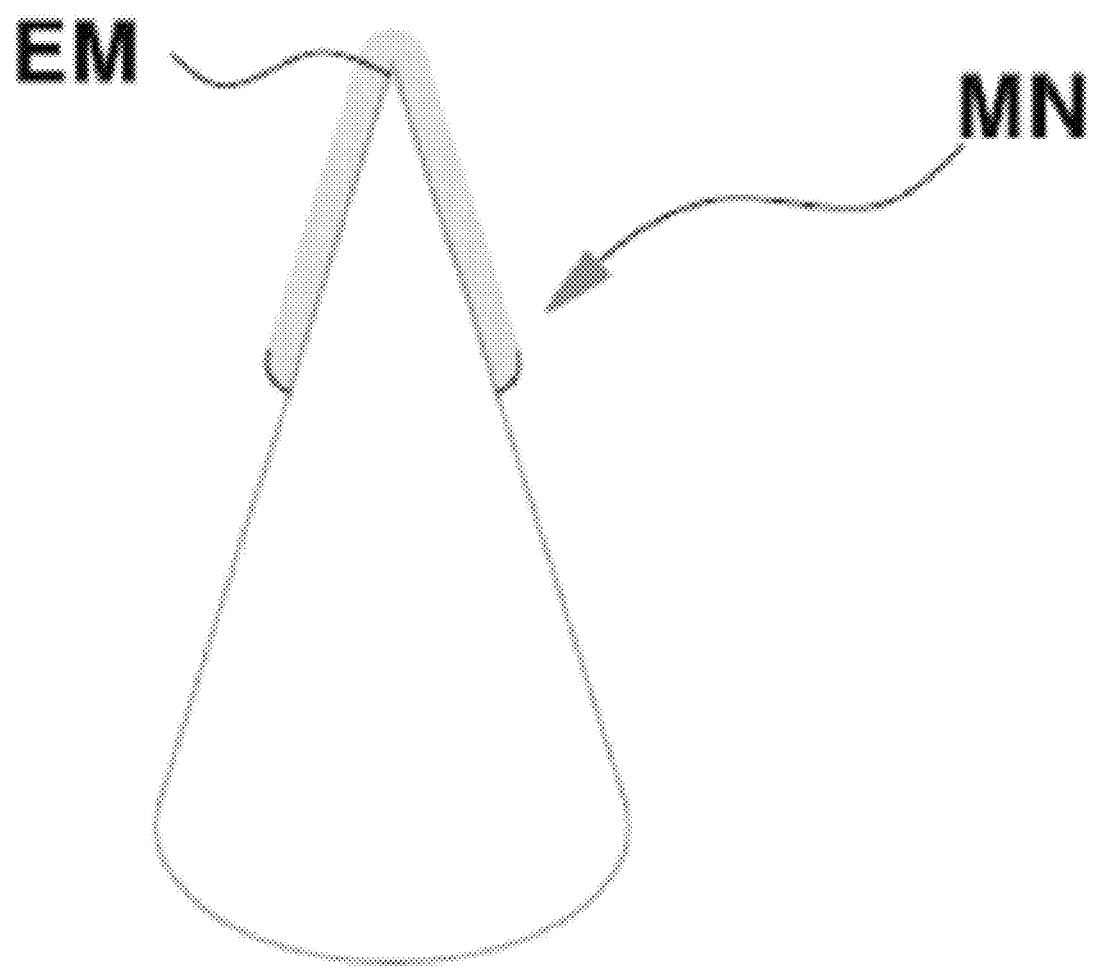

FIG. 1A is a perspective view of a microneedle patch according to an embodiment of the present invention, FIG. 1B shows side views of the microneedle patch according to different embodiments of the present invention, and FIGS. 2A and 2B are views illustrating one microneedle among a plurality of microneedles of the microneedle patch according to an embodiment of the present invention.

Referring to FIG. 1A, in an embodiment, a microneedle patch 1 may include a base layer BU including a mesh structure or auxetic materials having a negative Poisson's ratio and a microneedle array MN disposed on the base layer BU. The mesh structure or auxetic materials having the negative Poisson's ratio may expand or be enlarged in a direction perpendicular to an axis when a tensile force is applied in an axial direction and, conversely, may contract or be reduced in the direction perpendicular to the axis when a compressive force is applied in the axial direction. Refer to the following description of FIGS. 3A, 3B, 4A, and 4B for examples of the base layer BU having various mesh structures having a negative Poisson's ratio.

In an embodiment, microneedles may form the microneedle array MN in which the microneedles are spaced a predetermined distance apart and arranged in a first direction x and/or a second direction y. The predetermined distance may be in a range of 100 μm to 10 mm. In another embodiment, at least some of the microneedles may be randomly arranged on the base layer BU. Each of the plurality of microneedles may be joined to the base layer BU using an adhesive layer (not illustrated) to be fixed and supported.

Preferably, positions at which the plurality of microneedles are fixed and supported at the base layer BU are positions where little change occurs in the positions of the fixed microneedles even when the mesh structure of the base layer BU expands or contracts due to the tensile force or compressive force applied to the mesh structure. This is because, in this way, even when the mesh structure of the base layer BU is deformed due to the tensile force or compressive force applied to the mesh structure, changes in positions of the microneedles are also small in a state in which the microneedles are inserted into the skin, and thus detachment of some of the microneedles from the skin may be prevented. For example, microneedles may be disposed at intersection points of the mesh structure of the base layer. Also, linear portions connecting the microneedles MN on the mesh structure or linear portions connecting the intersection points of the mesh structure may have a zigzag or serpentine shape, and in this way, the microneedle patch 1 may be freely stretched or deformed when tissue between the microneedles inserted into the skin is stretched.

Referring to FIG. 1B, in an embodiment, a height of the microneedles MN may increase or decrease in a direction from a midpoint m of the base layer to an outer boundary thereof. In particular, in a case in which the microneedle patch 1 is attached to treat a portion of the skin that protrudes due to an inflammatory response such as acne, it may be easy to appropriately attach the microneedle patch 1 to the bump portion when the height of the microneedles MN is low around the midpoint m and increases in the direction from the midpoint m to the outer boundary. In another embodiment, the microneedles MN may not be present in a partial region around the midpoint m of the microneedle patch 1 and may only be present in a portion surrounding the partial region. According to an embodiment of the present invention, in a case in which the dermis region, especially a portion where a pain spot is present, is exposed due to a wound, the microneedle patch 1 may prevent the microneedles from coming in contact with the pain spot and causing severe pain.

Referring to FIGS. 2A and 2B, the plurality of microneedles may each have an upper end portion and a lower end portion and may be individualized from each other. FIGS. 2A and 2B show one microneedle among the plurality of microneedles. The microneedle MN is joined to the base layer BU, and of both end portions of the microneedle, one end portion joined to the base layer may be defined as the lower end portion, and the other end portion opposite the lower end portion may be defined as the upper end portion. In an embodiment, a diameter of the microneedle may decrease in a direction from the lower end portion to the upper end portion. For example, the upper end portion may be a sharp end portion, and the lower end portion may be a flat surface portion.

In an embodiment, the lower end portion may have a circular shape, a polygonal shape such as a triangular shape, a quadrangular shape, or a pentagonal shape, or a combination thereof. In another embodiment, in the microneedle MN, a portion at the lower end portion-side may be formed in the shape of a pillar with a constant diameter, and a portion at the upper end portion-side may have a conical shape, a polygonal pyramid shape such as a triangular pyramid shape or a quadrangular pyramid shape, or a combination thereof extending from the shape of the pillar. In still another embodiment, the microneedle MN may have the shape of a pillar with a constant diameter from the lower end portion to the upper end portion. In an embodiment of the present invention, in the case in which the upper end portion is a sharp end portion, when attaching the microneedle patch to a target site, the sharp end portion may pass through the epidermis and form a predetermined channel so that the microneedles may be easily inserted into the epidermis, and as will be described below, effective materials applied to any partial region of the microneedles may easily enter the dermis or body through the channel. Thus, it is possible to provide a microneedle patch that is pharmacologically or medically efficient.

In an embodiment, the base layer BU may pass the lower end portions of the microneedles neighboring each other among the plurality of microneedles MN and be joined to the lower end portions of the microneedles neighboring each other. The joining regions serve as the intersection points of the mesh structure, and the plurality of microneedles may be fixed to the intersection points of the mesh structure.

In an embodiment, the base layer BU may be formed of a water-soluble material and may be dissolved or degraded due to a moisture supplying member. The moisture supplying member may be selected from the group consisting of a moisture-containing sheet, a hydrogel sheet, a sheet mask, a moisturizing gel, a moisturizing cream, a toner, and an essence. Since the base layer BU reacts with moisture selectively absorbed from the outside and rapidly degrades, a user's discomfort due to the remaining base layer BU or a user's inconvenience of having to remove the base layer BU and wash off the residue with water may be prevented.

In an embodiment, the plurality of microneedles MN may include a biodegradable material. The biodegradable material may be a monosaccharide, a polysaccharide, a biodegradable hydrogel, a biodegradable polymer, or a combination thereof. For example, the biodegradable material may be: a bio-derived soluble material that is at least any one of chitosan, collagen, gelatin, hyaluronic acid (HA), alginic acid, pectin, carrageenan, chondroitin (sulfate), dextran (sulfate), polylysine, carboxymethyl titine, fibrin, agarose, pullulan, and cellulose; a biocompatible material that is at least any one of polyvinylpyrrolidone (PVP), polyethylene glycol (PEG), polyvinyl alcohol (PVA), hydroxypropyl cellulose (HPC), hydroxyethyl cellulose (HEC), hydroxypropyl methylcellulose (HPMC), sodium carboxymethyl cellulose, polyalcohol, gum arabic, alginate, cyclodextrin, dextrin, glucose, fructose, starch, trehalose, glucose, maltose, lactose, lactulose, fructose, turanose, melitose, melezitose, dextran, sorbitol, xylitol, pallatinite, polylactic acid, polyglycolic acid, polyethylene oxide, polyacrylic acid, polyacrylamide, polymethacrylic acid, and polymaleic acid; a derivative of any of the above-listed materials; or a mixture thereof. The above-listed materials are non-limiting examples and do not limit the present invention, and all kinds of materials that are harmless to the living body and can naturally degrade in the living body may be applied. According to an embodiment of the present invention, since the materials constituting the plurality of microneedles are biodegradable, the microneedles may be kept inside the body without being taken out of the body after use, and thus, it is possible to obtain a high level of effect of the plurality of microneedles or effective materials inside the plurality of microneedles just by a simple method of separating or removing the base layer from the plurality of microneedles during use.

In another embodiment, the plurality of microneedles may be formed of HA. The HA is a biosynthetic material that is present in a large amount in a living body and is used in cosmetic products or sheet masks due to having a moisturizing effect when applied to the skin. According to an embodiment of the present invention, since the plurality of microneedles themselves are formed of HA, even when other effective materials are not added into the microneedles, the microneedles may have a moisturizing effect when inserted into skin tissue, and it is possible to obtain a significant moisturizing effect and/or a cosmetic effect due to the moisturizing effect even without a device such as an injection needle that causes pain.

In an embodiment, the plurality of microneedles may include, in at least any portion thereof, a plurality of pharmaceutically, medically, or cosmetically effective materials EM. For example, the effective materials may be, but are not limited to, proteins, peptides, genes, antibodies, anesthetics, insulin, vaccines, polysaccharides, synthetic organic compounds, synthetic inorganic compounds, or cosmetic components such as skin lightening agents, fillers, wrinkle reducing agents, or antioxidants.

Referring to FIG. 2A, in an embodiment, the effective material EM may be colloid particles that disperse in a solvent forming the microneedle MN. The particles themselves may be the effective material EM or may include a coating material carrying the effective material EM. A concentration of the particles in the upper end portion of the microneedle MN may be higher than a concentration of the particles in the lower end portion of the microneedle. According to an embodiment of the present invention, since the effective material EM is intensively distributed in the upper end portion, it is possible to obtain a sufficient effect of the effective material EM even when only a partial region of the microneedle MN that includes the upper end portion is inserted into the target site instead of the entire microneedle MN, ranging from the upper end portion to the lower end portion, being inserted into the target site, and there is an economic advantage because the maximum effect can be obtained with a small amount of effective material EM.

In another embodiment, the effective material EM may be dissolved in the microneedle MN. The effective material EM may be dissolved in the material constituting the microneedle MN, such as any of the above-listed biodegradable materials, to form the microneedle MN. The effective material EM may be evenly dissolved in the material constituting the microneedle MN or may be intensively distributed in the upper end portion of the microneedle MN, like the particles described above.

In an embodiment, a first group of microneedles among the plurality of microneedles may include a first effective material among the plurality of effective materials, and a second group of microneedles that is different from the first group may include a second effective material among the plurality of effective materials.

Referring to FIG. 2B, in an embodiment, the pharmaceutically, medically, or cosmetically effective materials EM may be coated on the microneedles MN. The effective materials EM may be coated on the entire microneedles MN or may only be coated on any one portion of the upper end portion of each microneedle MN. Alternatively, the first effective material may be coated on any one portion of the upper end portion of each microneedle MN, and the second effective material may be coated below the portion coated with the first effective material.

Figure 3A:
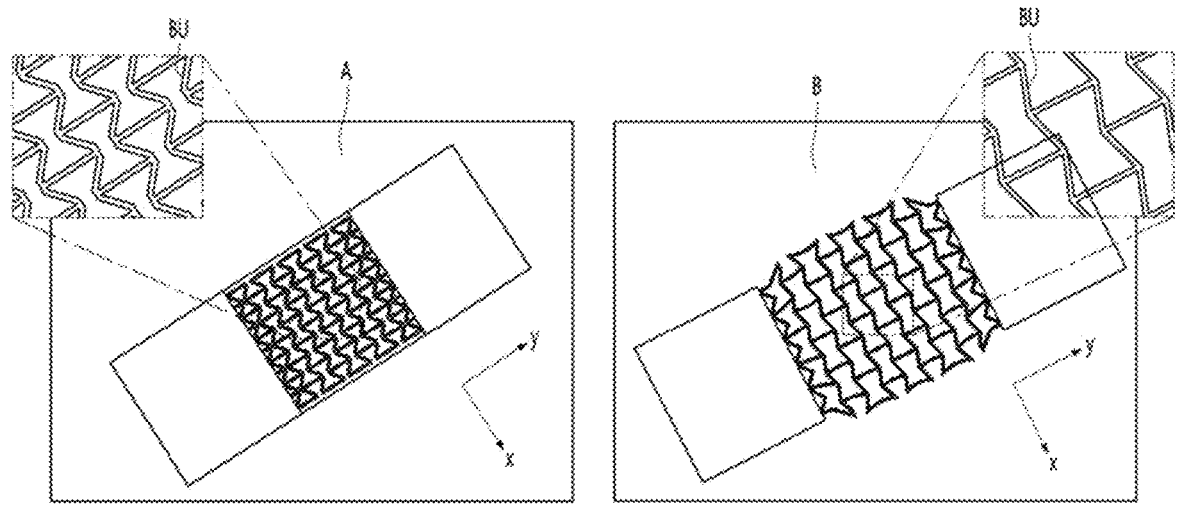
Figure 3B:
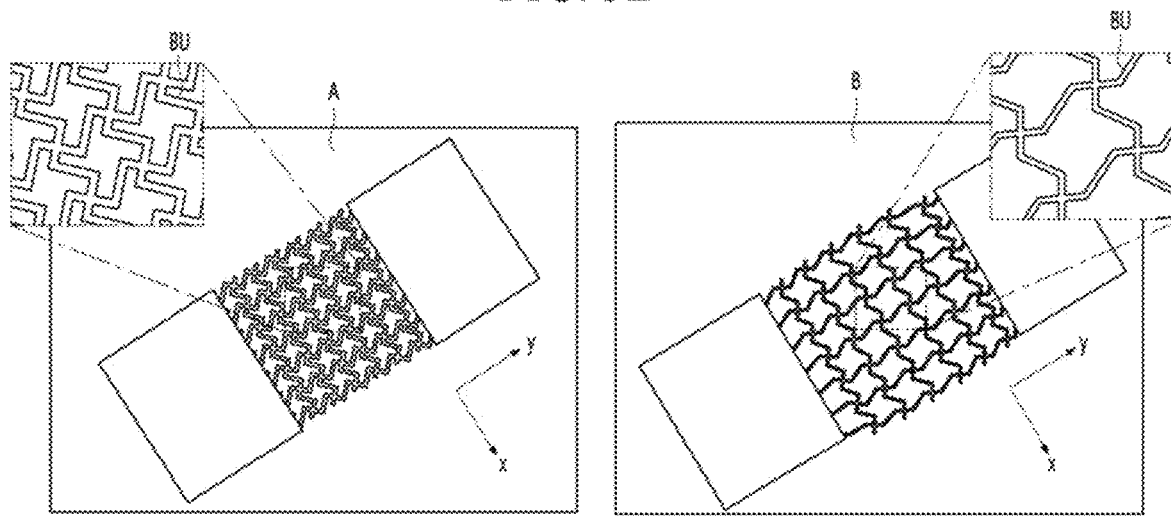

FIGS. 3A and 3B are views illustrating a two-dimensional mesh structure having a negative Poisson's ratio according to various embodiments of the present invention. FIG. 3A shows a state of the mesh structure having a negative Poisson's ratio before a tensile force is applied to the base layer BU having the mesh structure having a negative Poisson's ratio, and FIG. 3B shows a state of the mesh structure having a negative Poisson's ratio after a tensile force is applied to the base layer BU having the mesh structure having a negative Poisson's ratio.

Referring to FIG. 3A, the mesh structure having a negative Poisson's ratio may include a mesh structure that is patterned as a two-dimensional re-entrant honeycomb structure. Although not illustrated, the microneedles MN may be jointed to intersection points of the mesh structure. In another embodiment, the microneedles MN may be disposed between the intersection points of the mesh structure. When a tensile force is applied to the mesh structure having a negative Poisson's ratio, since the mesh structure is stretched in both axial and horizontal directions, it is possible to reduce the concentration of stress on weak portions of the mesh structure.

Referring to FIG. 3B, the mesh structure having a negative Poisson's ratio may include a mesh structure that is patterned as a two-dimensional cut missing rib structure. Although not illustrated, the microneedles MN may be jointed to intersection points of the mesh structure. In another embodiment, the microneedles MN may be disposed between the intersection points of the mesh structure. As in FIG. 3A, when a tensile force is applied to the mesh structure having a negative Poisson's ratio, since the mesh structure is stretched in both axial and horizontal directions, it is possible to reduce the concentration of stress on weak portions of the mesh structure.

Consequently, the microneedle array MN disposed on the mesh structure having a negative Poisson's ratio may have tensile deformation in a first direction (y-axis) due to a tensile force and tensile deformation in a second direction (x-axis) different from the first direction (y-axis) or may have compressive deformation in the first direction (y-axis) due to a compressive force and compressive deformation in the second direction (x-axis) different from the first direction (y-axis).

Figure 4A:
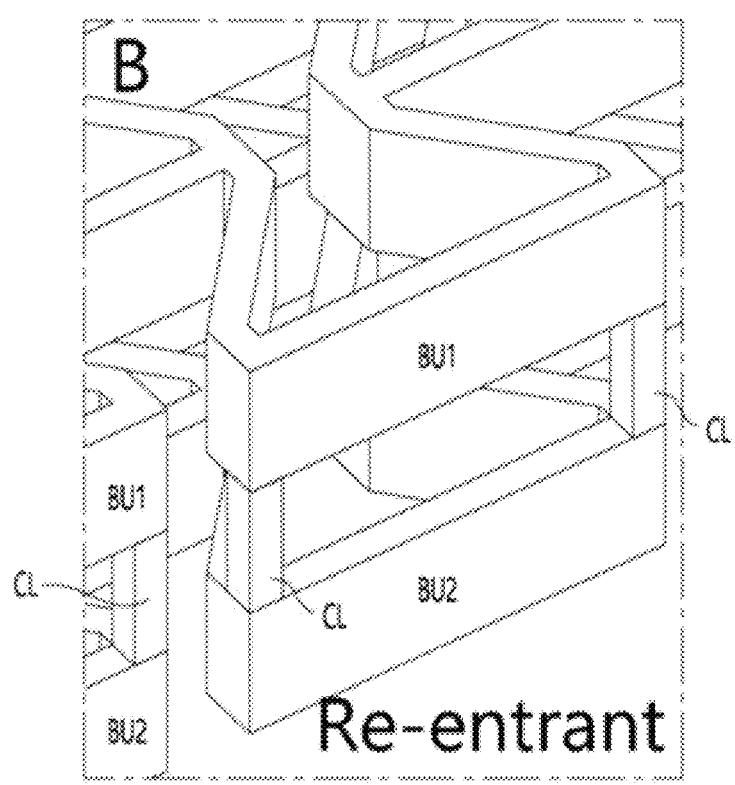
Figure 4B:
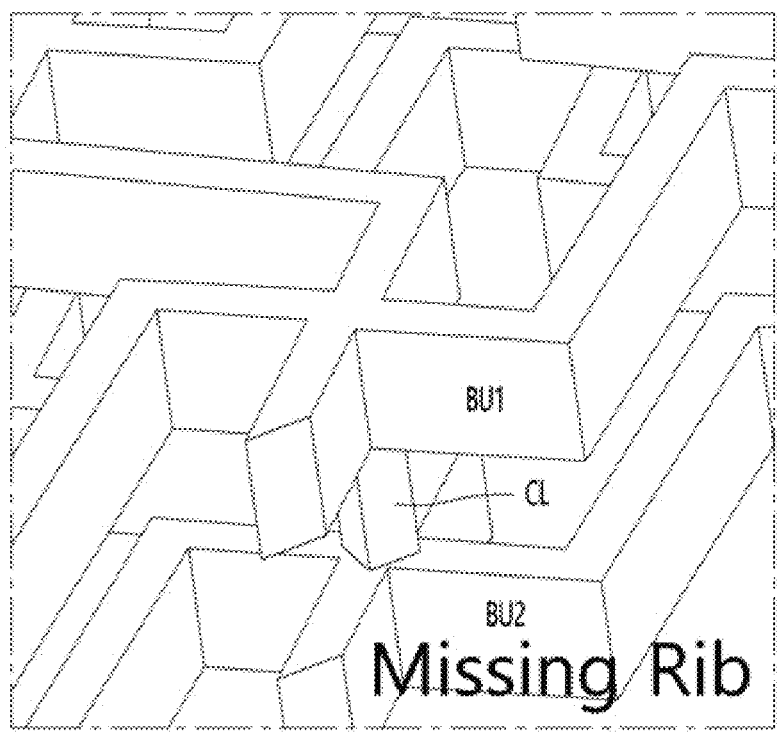

FIGS. 4A and 4B are views illustrating a three-dimensional mesh structure having a negative Poisson's ratio according to various embodiments of the present invention.

Referring to FIG. 4A, a base layer BU having a three-dimensional mesh structure may include a plurality of two-dimensional re-entrant honeycomb structures BU1 and BU2 which are spaced apart and stacked and a plurality of interlayer connecting portions CL connecting the two-dimensional re-entrant honeycomb structures BU1 and BU2 which are spaced apart and stacked. Although not illustrated, the microneedles MN may be joined to intersection points of the two-dimensional re-entrant honeycomb structure BU1. In another embodiment, the microneedles MN may be disposed between the intersection points of the two-dimensional re-entrant honeycomb structure BU1.

Referring to FIG. 4B, a base layer BU having a three-dimensional mesh structure may include a plurality of two-dimensional cut missing rib structures BU1 and BU2 which are spaced apart and stacked and a plurality of interlayer connecting portions CL connecting the two-dimensional cut missing rib structures BU1 and BU2 which are spaced apart and stacked. Although not illustrated, the microneedles MN may be joined to intersection points of the two-dimensional cut missing rib structure BU1. In another embodiment, the microneedles MN may be disposed between the intersection points of the two-dimensional cut missing rib structure BU1.

In still another embodiment, the two-dimensional re-entrant honeycomb structures and the two-dimensional cut missing rib structures may be spaced apart and stacked alternately, and the two-dimensional re-entrant honeycomb structures and the two-dimensional cut missing rib structures may be connected through a plurality of interlayer connecting portions CL. In FIGS. 4A and 4B, the interlayer connecting portion CL may have the shape of a post in order to allow the mesh structures BU1 and BU2 to be spaced apart. In FIGS. 4A and 4B, the mesh structures BU1 and BU2 may be stacked to be horizontal to the ground, but in yet another embodiment, the mesh structures BU1 and BU2 may also be arranged to be vertical to the ground to form the three-dimensional mesh structure having a negative Poisson's ratio.

FIGS. 5A, 5B, 6A, and 6B are views illustrating an auxetic structure having a negative Poisson's ratio according to yet another embodiment of the present invention.

Figure 6A:
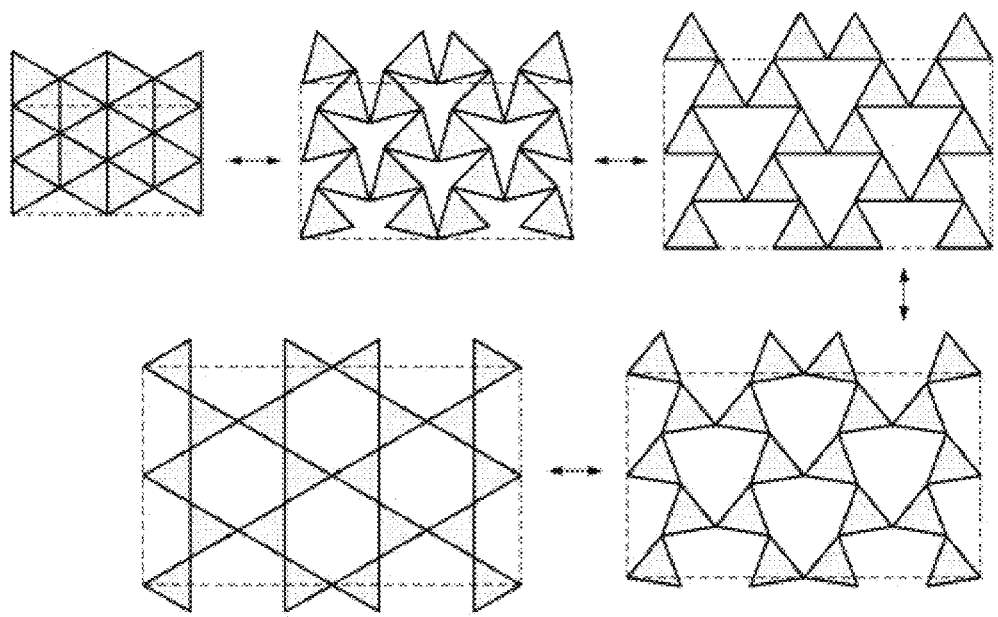
Figure 6B:
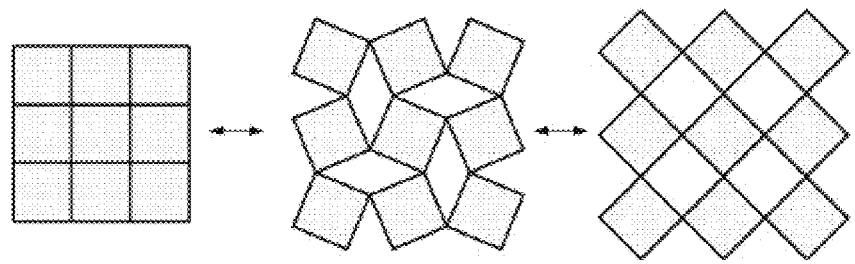

Referring to FIGS. 5A and 5B, the auxetic structure may include a chiral structure, and the structure has a form in which linear elements are arranged in a spiral shape on outer boundaries of circular or polygonal rigid bodies. Referring to FIGS. 6A and 6B, the auxetic structure may include a rotating structure, and the structure has a form in which polygonal rigid bodies are connected to each other at vertices thereof.

However, the present invention is not limited to the mesh structures having a negative Poisson's ratio that are illustrated in FIGS. 3A to 6B, and any structure having characteristics of the auxetic materials or auxetic structure may be applied.

Figure 7:
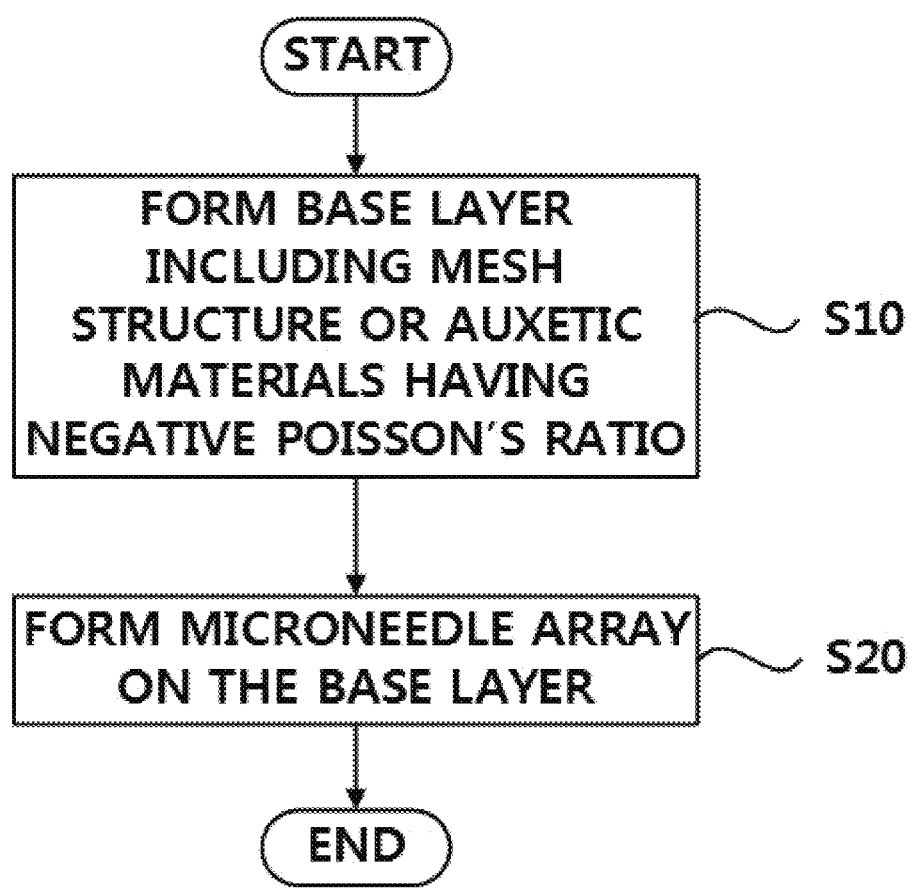
FIG. 7 is a flowchart of a method of fabricating a microneedle patch according to an embodiment of the present invention.

FIG. 7 is a flowchart for describing a method of fabricating a microneedle patch according to an embodiment of the present invention.

Referring to FIG. 7, a method of fabricating a microneedle patch may include forming a base layer including a mesh structure or auxetic materials having a negative Poisson's ratio (S10) and forming a microneedle array on the base layer (S20).

In implementation, a microneedle array including a plurality of microneedles may be formed, and then lower end surfaces of the microneedles may be connected to form a base layer including a mesh structure or auxetic materials having a negative Poisson's ratio.

The forming of the base layer (S10) or the forming of the microneedle array (S20) may be performed by 3D printing, laser cutting, molding, or a combination thereof. In an embodiment, the 3D printing may include stereolithography (SLA), digital micromirror device-based projecting printing (DMD-PP), two-photon polymerization (2PP), fused deposition modelling (FDM), inkjet, bioprinting, selective laser melting (SLM), electron beam melting (EBM), or a combination thereof. However, the 3D printing of the present invention is not limited thereto.

According to an embodiment of the present invention, the base layer BU having an auxetic structure may be formed in any size and shape using 3D printing technology, and thus the microneedle patch may be fabricated to be easily attached to various target sites such as under an eye, around the mouth, an arm, a shoulder, and the abdomen.

Since the above-described mesh structures having a negative Poisson's ratio have various advantageous properties such as improved shear modulus, fracture toughness, piezoelectric property, indentation resistance, thermal shock resistance, shock absorption, wear resistance, and energy absorption, in particular, there are advantages in that contact stress is reduced in a case in which two objects come into contact and receive force, and stress concentration on weak portions of the objects is reduced.

Therefore, by utilizing the base layer BU having the mesh structure having a negative Poisson's ratio of the present invention, the microneedle patch 1 may be flexibly attached to the skin, and even when the microneedle patch 1 attached to the skin is stretched or compressed, some of the microneedles MN may stably maintain a state of being inserted into the skin instead of being detached from a curved skin surface.

Second Embodiment

Figure 8:
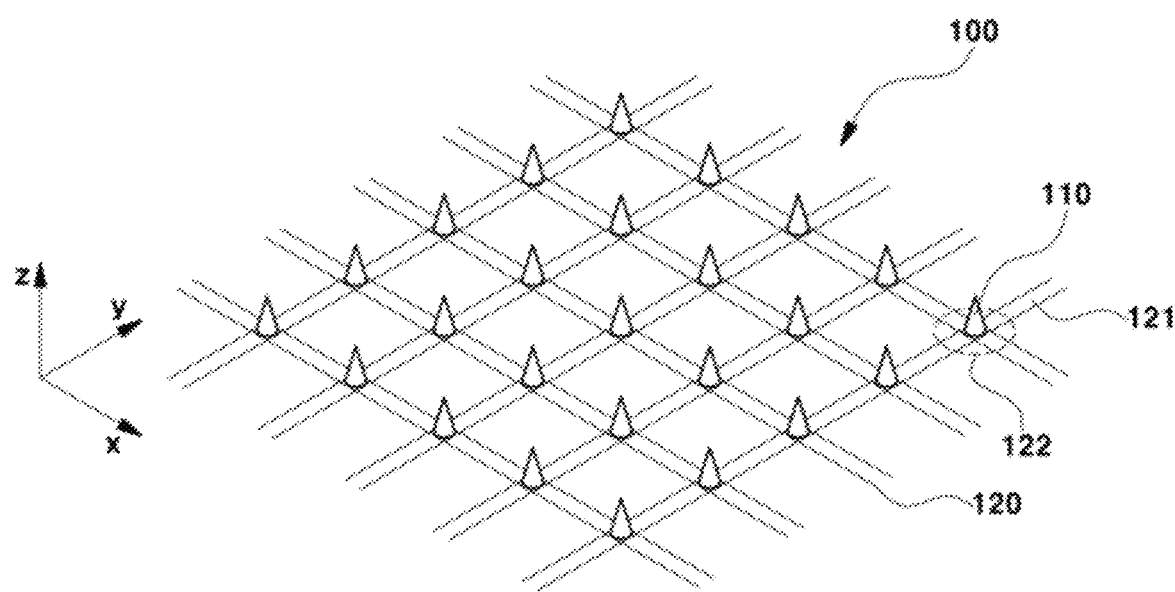
FIG. 8 is a perspective view of a microneedle patch according to an embodiment of the present invention.

FIG. 8 is a perspective view of a microneedle patch 100 according to the present embodiment.

Referring to FIG. 8, in an embodiment, the microneedle patch 100 may include a plurality of microneedles 110 and a base layer 120 joined to base portions 111 of the plurality of microneedles 110. The microneedles 110 may be spaced a predetermined distance apart and arranged in a first direction x and/or a second direction y to form an array of the microneedles 110. The predetermined distance may be in a range of 100 μm to 10 mm. In another embodiment, at least some of the microneedles 110 may be randomly arranged on the base layer 120. Each of the plurality of microneedles 110 may be joined to the base layer 120 so as to be fixed and supported.

In an embodiment, the base layer 120 may include linear portions 121 that pass the base portions 111 of the microneedles 110 neighboring each other among the plurality of microneedles 110 and are joined to the base portions 111. The linear portions 121 may at least partially intersect each other to form the base layer 120 having a planar structure. In an embodiment, the linear portions 121 may be a fibrous structure formed by processing a precursor of the base layer 120. For example, at least some of the linear portions 121 may have a linear shape while the remaining linear portions 121 have a curved shape having a predetermined curvature, or the shape of the linear portions 121 may be a combination of linear shapes in which at least one or more bent portions are present.

In an embodiment, a plurality of through-pores that pass through the base layer 120 may be formed between the linear portions 121. For example, the base layer 120 may have a mesh structure. In another embodiment, the base layer 120 may also have a gyroid structure. The through-pores may have a circular shape, a polygonal shape such as a triangular shape or a quadrangular shape, or an elliptical shape. Although not illustrated, in another embodiment, the through-pores may have a slit-shaped linear pattern, a meander pattern, a wavy pattern, or a composite pattern in which linear structures or the above-listed patterns intersect each other. According to an embodiment of the present invention, since the plurality of through-pores are formed in the base layer 120, as compared to the case in which the through-pores are not present, the volume or area occupied by the linear portions 121 relative to the entire area of the base layer 120 is smaller, and the amount of moisture absorbed by the base layer 120 which is formed of a water-soluble material is smaller. Therefore, it is possible to prevent a side effect in which the base layer 120 absorbs moisture from the target site rather than providing moisture thereto.

In an embodiment, the plurality of microneedles 110 may be fixed at regions 122 where at least two or more linear portions 121 among the plurality of linear portions 121 intersect. Two linear portions 121, three linear portions 121, or four or more linear portions 121 may intersect in the regions 122 where the linear portions 121 intersect. The regions 122 where the linear portions 121 intersect may have a larger thickness than regions where the linear portions 121 do not intersect and thus support the microneedles 110 with a larger support force. Since non-intersecting regions of the linear portions 121 may be easily stretched, it is possible to provide the microneedle patch 100 having high flexibility.

Figure 9:
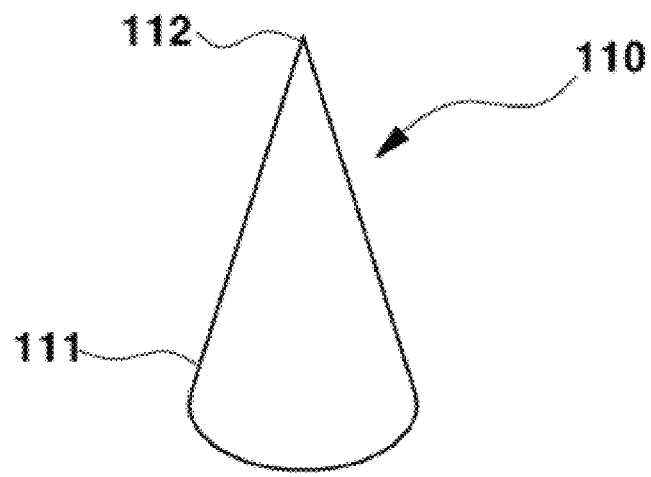
FIG. 9 is a view illustrating a microneedle according to an embodiment of the present invention.

FIG. 9 is a view illustrating the microneedle 110 according to an embodiment of the present invention.

Referring to FIG. 9, in an embodiment, the plurality of microneedles 110 may each have an upper end portion 112 and the base portion 111 and may be individualized from each other. FIG. 9 illustrates one microneedle 110 among the plurality of microneedles 110. The microneedle 110 is joined to the base layer 120, and of both end portions of the microneedle 110, one end portion joined to the base layer 120 may be defined as the base portion 111, and the other end portion opposite the base portion 111 may be defined as the upper end portion 112. In an embodiment, a diameter of the microneedle 110 may decrease in a direction from the base portion 111 to the upper end portion 112. For example, the upper end portion 112 may be a sharp end portion, and the base portion 111 may be a flat surface portion.

In an embodiment, a cross-section of the base portion 111-side end portion may have a circular shape, a polygonal shape such as a triangular shape, a quadrangular shape, or a pentagonal shape, or a combination thereof. In another embodiment, in the microneedle 110, a portion at the base portion 111-side may be formed in the shape of a pillar with a constant diameter, and a portion at the upper end portion 112-side may have a conical shape, a polygonal pyramid shape such as a triangular pyramid shape or a quadrangular pyramid shape, or a combination thereof extending from the shape of the pillar. In still another embodiment, the microneedle 110 may have the shape of a pillar with a constant diameter from the base portion 111 to the upper end portion 112. In an embodiment of the present invention, in the case in which the upper end portion 112 is a sharp end portion, when attaching the microneedle patch 100 to a target site, the sharp end portion may pass through the epidermis and form a predetermined channel so that the microneedles 110 may be easily inserted into the epidermis, and as will be described below, effective materials 130 applied to any partial region of the microneedles 110 may easily be delivered to the dermis or body through the channel. Thus, it is possible to provide the microneedle patch 100 that is pharmacologically or medically efficient.

In an embodiment, the plurality of microneedles 110 may include a biodegradable material. The biodegradable material may be a monosaccharide, a polysaccharide, a biodegradable hydrogel, a biodegradable polymer, or a combination thereof. For example, the biodegradable material may be: a bio-derived soluble material that is at least any one of chitosan, collagen, gelatin, hyaluronic acid (HA), alginic acid, pectin, carrageenan, chondroitin (sulfate), dextran (sulfate), polylysine, carboxymethyl titine, fibrin, agarose, pullulan, and cellulose; a biocompatible material that is at least any one of polyvinylpyrrolidone (PVP), polyethylene glycol (PEG), polyvinyl alcohol (PVA), hydroxypropyl cellulose (HPC), hydroxyethyl cellulose (HEC), hydroxypropyl methylcellulose (HPMC), sodium carboxymethyl cellulose, polyalcohol, gum arabic, alginate, cyclodextrin, dextrin, glucose, fructose, starch, trehalose, glucose, maltose, lactose, lactulose, fructose, turanose, melitose, melezitose, dextran, sorbitol, xylitol, pallatinite, polylactic acid, polyglycolic acid, polyethylene oxide, polyacrylic acid, polyacrylamide, polymethacrylic acid, and polymaleic acid; a derivative of any of the above-listed materials; or a mixture thereof. The above-listed materials are non-limiting examples and do not limit the present invention, and all kinds of materials that are harmless to the living body and can naturally degrade in the living body may be applied. According to an embodiment of the present invention, since the materials constituting the plurality of microneedles 110 are biodegradable, the microneedles 110 may be kept inside the body without being taken out of the body after use, and thus, it is possible to obtain a high level of effect of the plurality of microneedles 110 or the effective materials 130 inside the plurality of microneedles 110 just by a simple method of separating or removing the base layer 120 from the plurality of microneedles 110 during use.

In another embodiment, the plurality of microneedles 110 may be formed of HA. The HA is a biosynthetic material that is present in a large amount in a living body and is used in cosmetic products or sheet masks due to having a moisturizing effect when applied to the skin. According to an embodiment of the present invention, since the plurality of microneedles 110 themselves are formed of HA, even when other effective materials 130 are not added into the microneedles 110, the microneedles 110 may have a moisturizing effect when inserted into skin tissue, and it is possible to obtain a significant moisturizing effect and/or a cosmetic effect due to the moisturizing effect even without a device such as an injection needle that causes pain.

FIGS. 10A to 10D are views illustrating a structure of the base layer 120 according to various embodiments of the present invention.

Figure 10A:
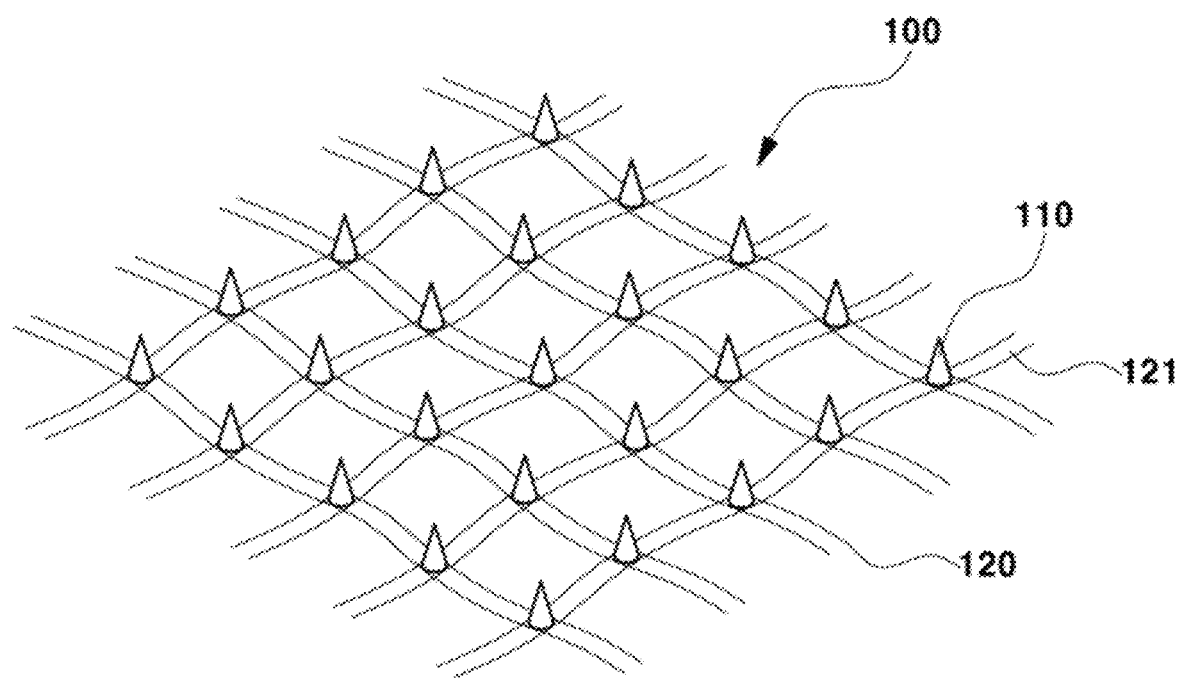
FIGS. 10A to 10D are views illustrating a structure of a base layer according to various embodiments of the present invention.

Referring to FIG. 10A, in an embodiment, at least some of the linear portions 121 may have a curved shape. For example, some of the linear portions 121 may have a meander structure or a spring structure. In the case in which the linear portions 121 have the curved structure, even when the base layer 120 partially stretches or contracts and mechanical deformation occurs, due to impact-absorbing action in which the curved shape of the portion where the deformation occurred stretches, mechanical deformation caused to another region may be reduced. Accordingly, there is an advantage in that it is easy to attach the microneedle patch 100 because, even when one portion of the microneedle patch 100 is attached first and then another portion thereof is stretched to attach the microneedle patch 100 to a target site that is curved, the portion that is attached first may not be detached.

Figure 10B:
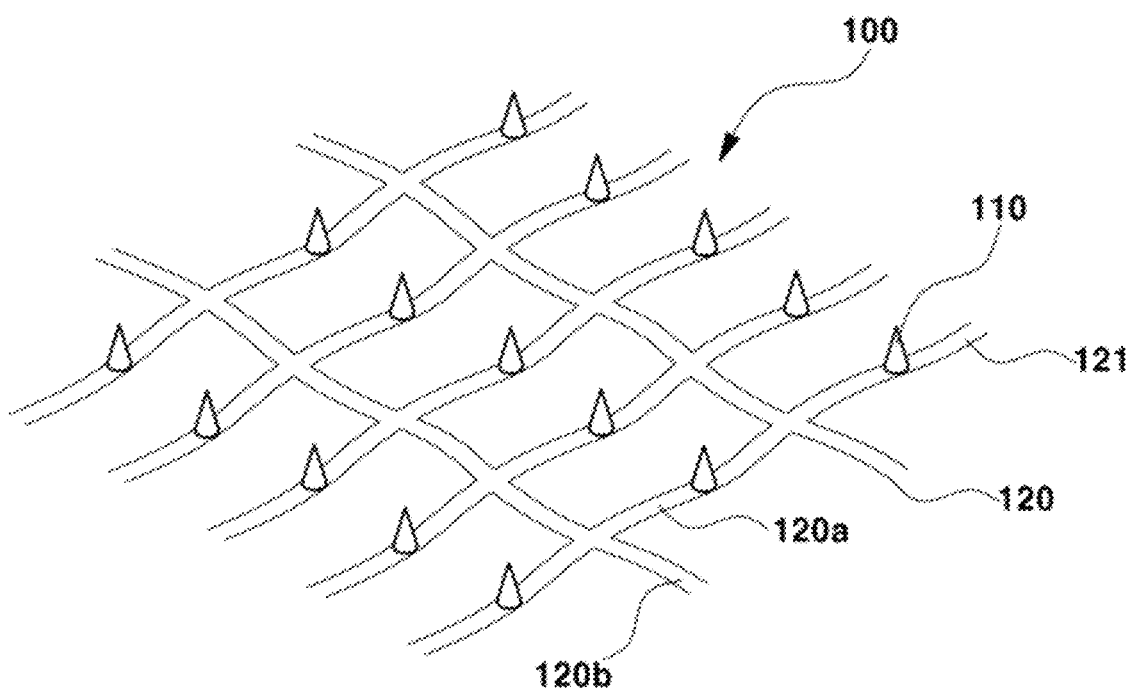

Referring to FIG. 10B, in an embodiment, the plurality of microneedles 110 may be joined to first linear portions 120a among the linear portions 121 constituting the base layer 120, and the remaining second linear portions 120b may connect and physically fix the first linear portions 120a to which the plurality of microneedles 110 are joined. Regions where the first linear portions 120a and the second linear portions 120b intersect may be separated from each other and joined or may be integrated without a boundary therebetween. In the case in which the second linear portions 120b have elasticity, the base layer 120 may have flexibility or elasticity and be easily deformed.

Figure 10C:
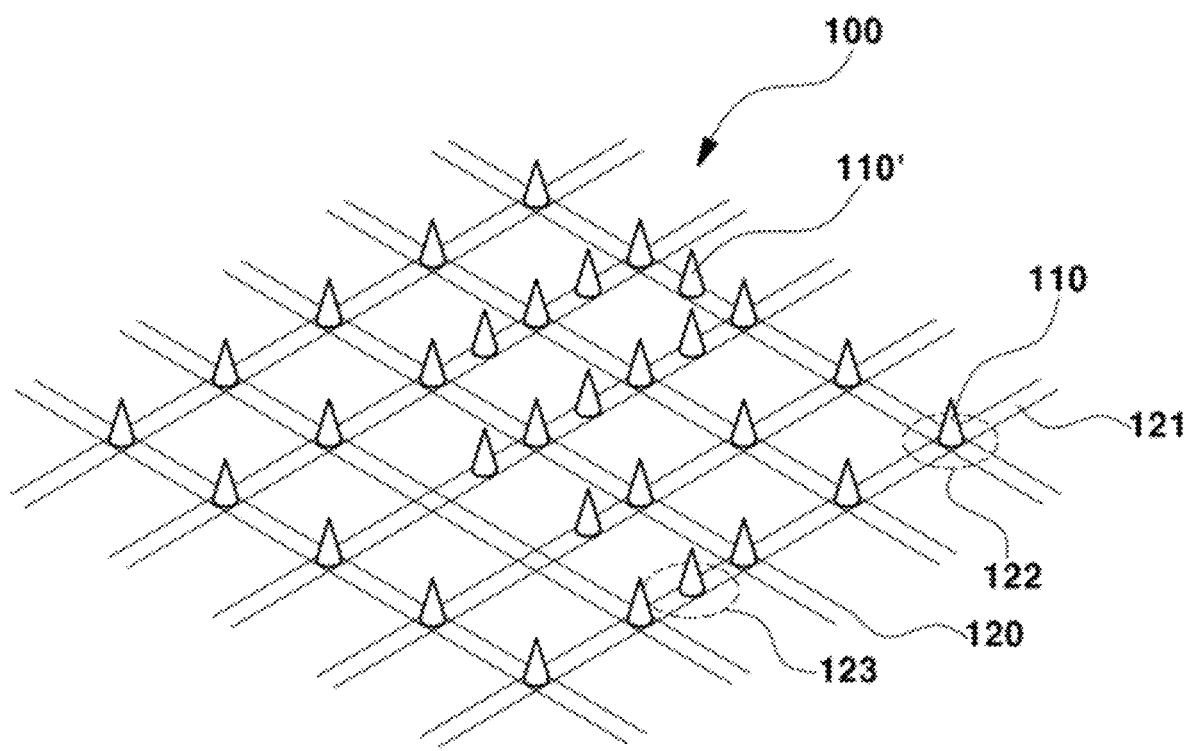

Referring to FIG. 10C, in an embodiment, some microneedles 110' among the plurality of microneedles 110 may be fixed at regions 123 where the linear portions 121 do not intersect and only one linear portion 121 is present. For example, some microneedles 110 among the plurality of microneedles 110 may be fixed at the regions 122 where the linear portions 121 intersect, and the remaining microneedles 110' may be fixed at the regions 123 where the linear portions 121 do not intersect. The microneedles 110 having a relatively large volume or weight may be fixed at the regions 122 where the linear portions 121 intersect, and the microneedles 110' which are relatively smaller may be fixed at the regions 123 where the linear portions 121 do not intersect. Also, since a thickness of the regions 122 where the linear portions 121 intersect is larger than a thickness of the regions 123 where the linear portions 121 do not intersect, a height of the microneedles 110 fixed at the regions 122 where the linear portions 121 intersect may be higher than a height of the microneedles 110' fixed at the regions 123 where the linear portions 121 do not intersect.

Figure 10D:
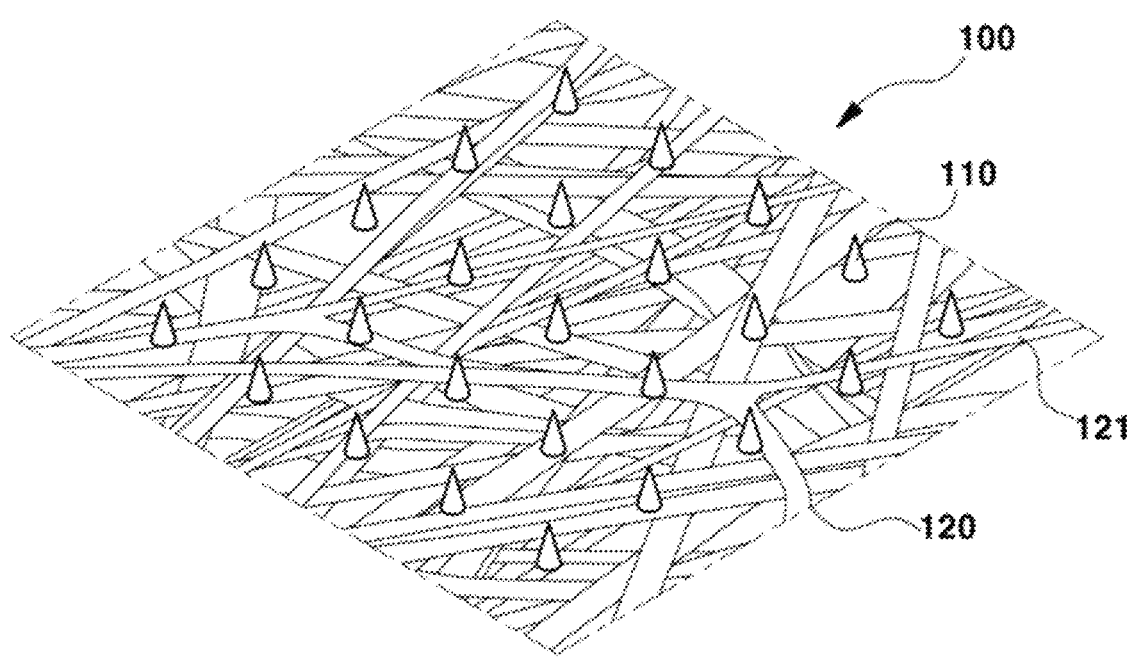

Referring to FIG. 10D, in an embodiment, the base layer 120 may have a nonwoven structure. Instead of intersecting each other and being fixed to form a woven fabric, the linear portions 121 may be randomly arranged and form a nonwoven structure. The base layer 120 may have a nonwoven structure in the case in which the linear portions 121 are formed using methods such as electrospinning in the process of forming the base layer 120 that will be described below or the base layer 120 is randomly printed without any particular regularity. According to an embodiment of the present invention, since the linear portions 121 may be randomly arranged, a speed of producing the base layer 120 may be improved, and production yield of the microneedle patch 100 may be increased.

In an embodiment, the microneedle patch 100 may further include an adhesive layer disposed between the base layer 120 and the plurality of microneedles 110. The adhesive layer may be formed of a biodegradable material. In another embodiment, the base portion 111 may be formed of the same material as the linear portion 121, and the base portion 111 and the linear portion 121 may be homogeneously joined. In still another embodiment, the base portion 111 may be formed of a different material from the linear portion 121, and the base portion 111 and the linear portion 121 may be heterogeneously joined.

In an embodiment, a thickness of the base layer 120 may be in a range of 0.01 mm to 1.5 mm. In the case in which the thickness is less than 0.01 mm, when attaching the microneedle patch 100, to which the plurality of microneedles 110 are joined, to a target site, the base layer 120 may be excessively deformed and cause difficulty in use, and it may be difficult to secure sufficient support force for the microneedles 110 to be inserted into the target site. In the case in which the thickness exceeds 1.5 mm, it may be difficult to obtain sufficient flexibility that allows the microneedle patch 100 to be stably attached when a target site is curved.

Figure 11:
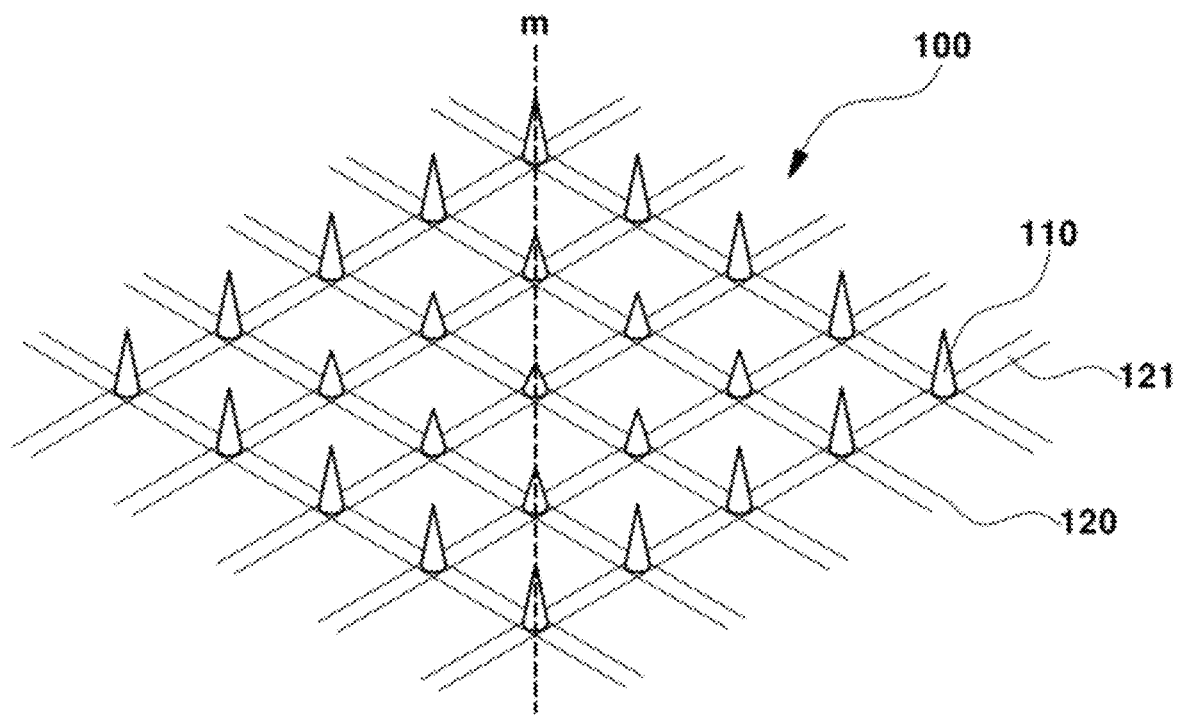
FIG. 11 is a perspective view of a microneedle patch according to another embodiment of the present invention.

FIG. 11 is a perspective view of the microneedle patch 100 according to another embodiment of the present invention.

In an embodiment, a height of the microneedles 110 may increase or decrease in a direction from a midpoint m of the base layer 120 to an outer boundary thereof. In particular, in the case in which the microneedle patch 100 is attached to treat a portion of the skin that protrudes due to an inflammatory response such as acne, it may be easy to appropriately attach the microneedle patch 100 to the protruding portion when the height of the microneedles 110 is low around the midpoint m and increases in the direction from the midpoint m to the outer boundary. In another embodiment, the microneedles 110 may not be present in a partial region around the midpoint m of the microneedle patch 100 and may only be present in a portion surrounding the partial region. According to an embodiment of the present invention, in the case in which the dermis region, especially a portion where a pain spot is present, is exposed due to a wound, the microneedle patch 100 may allow the microneedles 110 to only be inserted into portions where the pain spot is not present and prevent the microneedles 110 from coming in contact with the pain spot and causing severe pain.

Figure 12A:
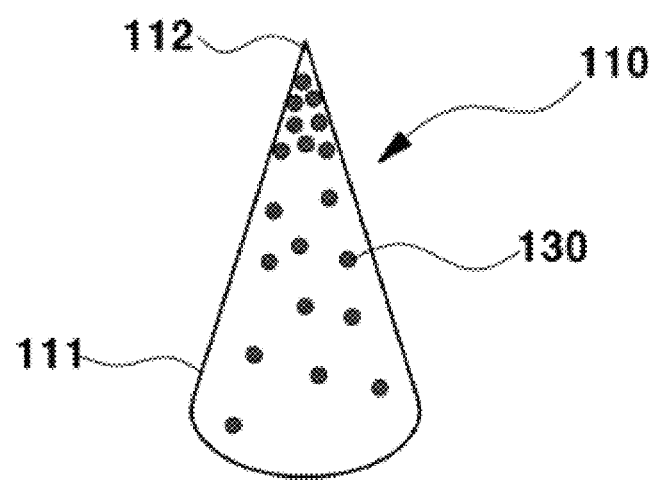
FIGS. 12A and 12B are views illustrating microneedles including effective materials according to an embodiment of the present invention.
Figure 12B:
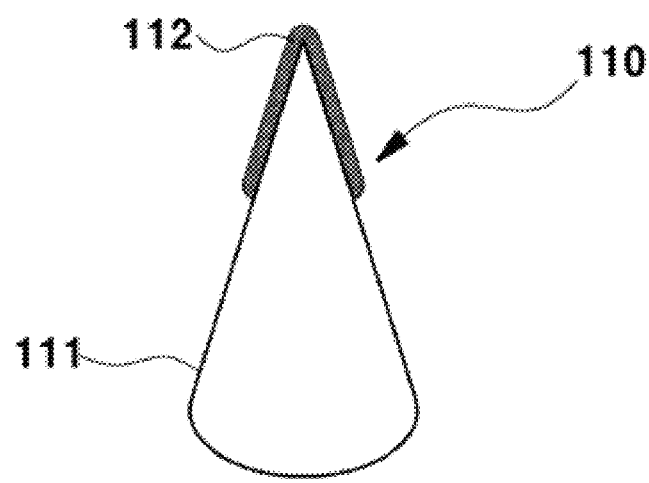

FIGS. 12A and 12B are views illustrating the microneedles 110 including the effective materials 130 according to an embodiment of the present invention.

In an embodiment, the plurality of microneedles 110 may include the effective materials 130 in at least any portion thereof. The effective materials 130 may be pharmaceutically, medically, or cosmetically effective materials 130. For example, the effective materials 130 may be, but are not limited to, proteins, peptides, genes, antibodies, anesthetics, insulin, vaccines, polysaccharides, synthetic organic compounds, synthetic inorganic compounds, or cosmetic components such as skin lightening agents, fillers, wrinkle reducing agents, or antioxidants.

Referring to FIG. 12A, in an embodiment, the effective material 130 may be colloid particles that disperse in a solvent forming the microneedle 110. The particles themselves may be the effective material 130 or may include a coating material carrying the effective material 130. A concentration of the particles in the upper end portion 112 of the microneedle 110 may be higher than a concentration of the particles in the base portion 111 of the microneedle 110. According to an embodiment of the present invention, since the effective material 130 is intensively distributed in the upper end portion 112, it is possible to obtain a sufficient effect of the effective material 130 even when only a partial region of the microneedle 110 that includes the upper end portion 112 is inserted into the target site instead of the entire microneedle 110, ranging from the upper end portion 112 to the base portion 111, being inserted into the target site, and there is an economic advantage because the maximum effect can be obtained with a small amount of effective material 130.

In order to allow the particles to be intensively distributed in the upper end portion 112, when fabricating the microneedle 110, in the case in which the upper end portion 112 is disposed at a lower portion and the base portion 111 is disposed at an upper portion in a mold 200 (see FIG. 16A) for forming the microneedle 110, the mold may be left for a predetermined amount of time to allow the particles to be intensively placed in the base portion 111, or a centrifuge may be used to allow the particles to be placed in the base portion 111 using a density difference between the particles and the material constituting the microneedle 110.

In another embodiment, the effective material 130 may be dissolved in the microneedle 110. The effective material 130 may be dissolved in the material constituting the microneedle 110, such as any of the above-listed biodegradable materials, to form the microneedle 110. The effective material 130 may be evenly dissolved in the material constituting the microneedle 110 or may be intensively distributed in the upper end portion 112 of the microneedle 110, like the particles described above.

Referring to FIG. 12B, in an embodiment, the pharmaceutically, medically, or cosmetically effective materials 130 may be coated on the microneedles 110. The effective materials 130 may be coated on the entire microneedles 110 or may only be coated on any one portion of the upper end portion 112 of each microneedle 110. Alternatively, a first effective material 130 may be coated on any one portion of the upper end portion 112, and a second effective material 130 may be coated below the portion coated with the first effective material 130.

Figure 13:
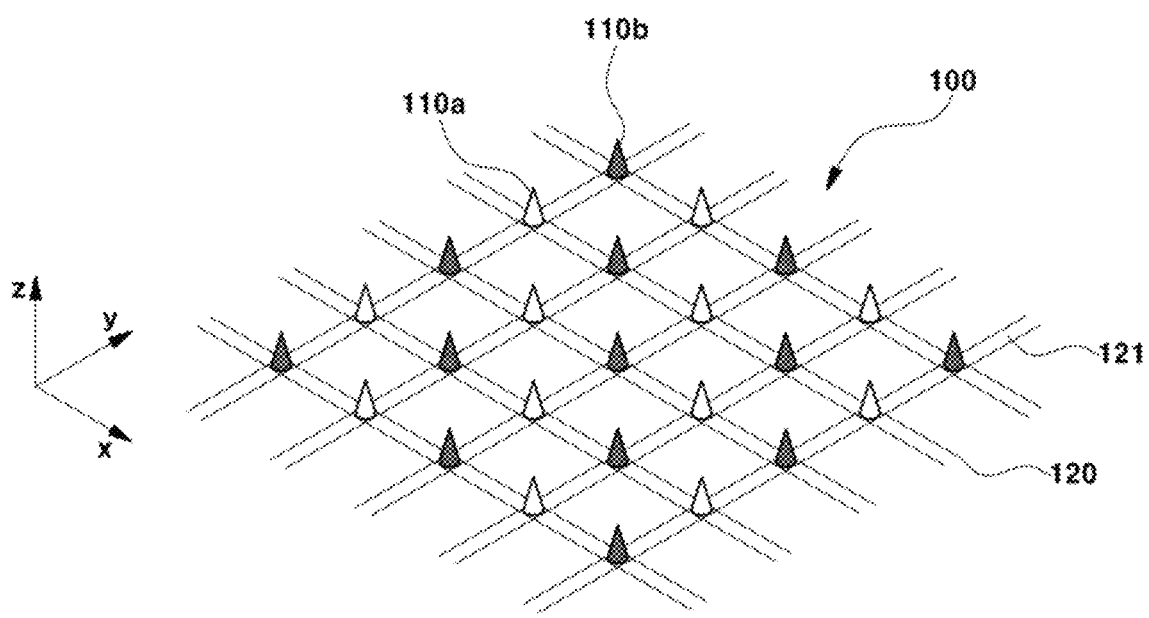
FIG. 13 is a perspective view of a microneedle patch according to still another embodiment of the present invention.

FIG. 13 is a perspective view of the microneedle patch 100 according to still another embodiment of the present invention.

Referring to FIG. 13, in an embodiment, the microneedle patch 100 may further include a plurality of kinds of effective materials 130 placed in at least any portion of the plurality of microneedles 110. For example, in the case in which the microneedle patch 100 is used for a cosmetic purpose, the effective materials 130 may include skin lightening agents, fillers, wrinkle reducing agents, or antioxidants, and in the case in which the microneedle patch 100 is used for a medical purpose, the effective materials 130 may include anesthetics, insulin, or vaccines. A first group 110a among the plurality of microneedles 110 may include a first effective material 130 among the plurality of kinds of effective materials 130, and a second group 110b different from the first group may include a second effective material 130 among the plurality of kinds of effective materials 130. The first group 110a and the second group 110b may be alternately arranged in the first direction x and/or the second direction y. Alternatively, only the first group 110a may be disposed in a partial region of the base layer 120, and only the second group 110b may be disposed in a region different from the partial region.

Figure 14A:
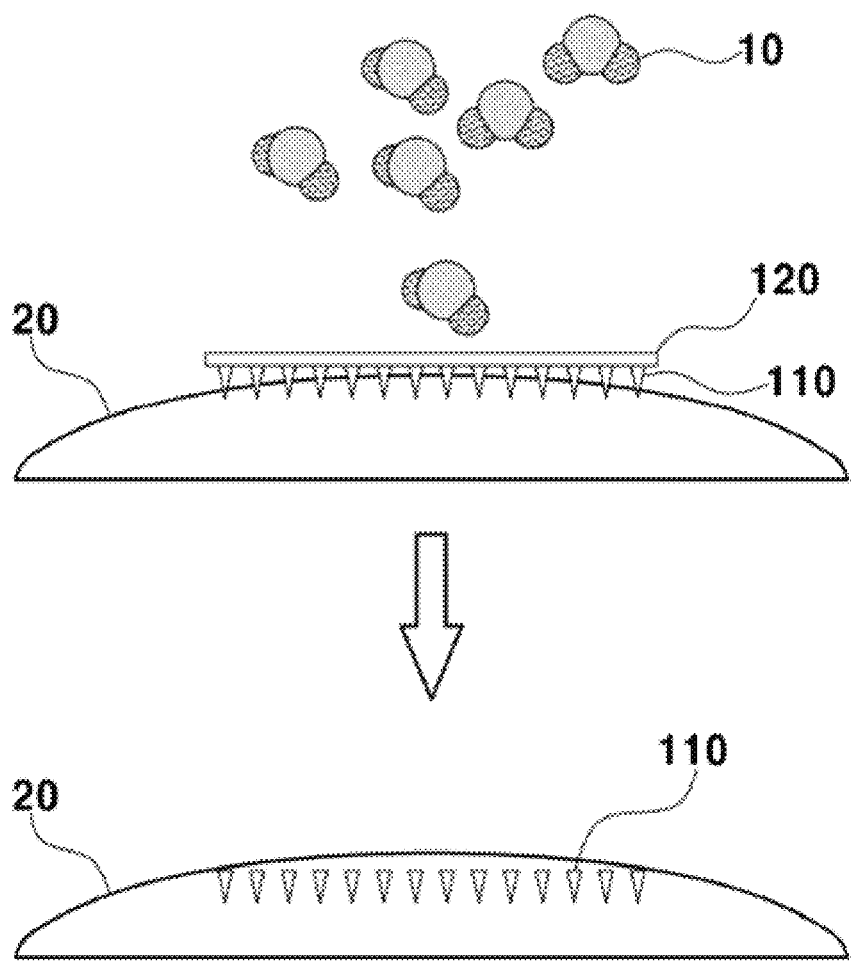
FIG. 14A is a view illustrating mechanism of the microneedle patch according to an embodiment of the present invention.

FIG. 14A is a view illustrating action of the microneedle patch 100 according to an embodiment of the present invention, and FIG. 14B is a view illustrating how to use the microneedle patch 100 according to an embodiment of the present invention.

Referring to FIG. 14A, the drawing above the arrow shows a state immediately after the microneedle patch 100 is attached to a target site, and the drawing below the arrow shows a state in which the microneedles 110 are inserted into the target site after moisture is supplied to the microneedle patch 100 and the base layer 120 degrades. In an embodiment, the base layer 120 of the microneedle patch 100 may be formed of a water-soluble material. The water-soluble material may include PEG, HA, agar, gelatin, carrageenan, PVA, PVP, polyacrylic acid, polyacrylate, or a combination thereof. The base layer 120 may include a water-soluble material and absorb moisture 10 and degrade, and when the base layer 120 degrades, the microneedles 110 supported by the base layer 120 may remain in a target site 20, be inserted into the epidermis, or degrade in the epidermis.

In an embodiment, after the microneedle patch 100 is attached to the target site 20, a sheet mask (not illustrated) may be additionally applied on the microneedle patch 100. Since the sheet mask contains a large amount of moisture 10 to provide a moisturizing effect, the sheet mask may provide a sufficient amount of moisture for degradation of the base layer 120. Also, here, in the case in which the base layer 120 is formed of the linear portions 121 and includes through-pores formed between the linear portions 121, moisture and/or nutritional components contained in the sheet mask may easily pass through the base layer 120 and be diffused to the target site through the through-pores. According to an embodiment of the present invention, since the process of removing the microneedle patch 100 after use is omitted and the microneedle patch 100 and the sheet mask are simultaneously applied, it is possible to obtain a significant cosmetic effect within a short time.

Referring to FIG. 14B, in an embodiment, a microneedle patch 100a that does not contain any effective material 130 may be used, or a microneedle patch 100b that contains a predetermined effective material 130 may be used, depending on target sites 20a and 20b to which the microneedle patch 100 will be applied. For example, one of the target sites may be a site that is oily and requires oil-free moisturizing, such as the T-zone which includes the forehead and nose, and the other target site may be a site that is less oily and prone to wrinkles and requires oil supply, such as an area under an eye or around the mouth. A cheek area 20a illustrated in FIG. 14B mainly requires moisturizing, and thus the microneedle patch 100a not containing any effective material 130 may be attached to the cheek area 20a. An around-the-mouth area 20b requires a large amount of oil, and thus the microneedle patch 100b that contains the effective material 130 containing nutritional components such as glycerol may be attached to the around-the-mouth area 20b.

FIG. 15 is a flowchart of a method of fabricating the microneedle patch 100 according to an embodiment of the present invention.

First, the plurality of microneedles 110 each having the upper end portion 112 and the base portion 111 and which are individualized from each other are prepared (S100). In an embodiment, the mold 200 (see FIG. 16A) for forming the microneedles 110 may be prepared, the material constituting the microneedles 110 may be applied to the mold 200, and then the material may be dried or heated to form the plurality of microneedles 110. The mold 200 may be an intaglio mold. The mold 200 may include poly-dimethylsiloxane (PDMS), polycaprolactone (PCL), polyester (PET), polyethylene (PE), polyurethane (PU), polyamide, or a combination thereof.

In an embodiment, an adhesive may be provided on a region where the microneedles 110 are present that is above the mold 200 in which the plurality of microneedles 110 are formed, and then, the base layer 120 that is completely formed may be provided and joined to the plurality of microneedles 110. The base layer 120 may be formed by electrospinning which will be described below, or a commercially available product may be purchased and used as the base layer 120. These are non-limiting examples, and various other known technologies relating to film or membrane formation may be used.

Figure 16A:
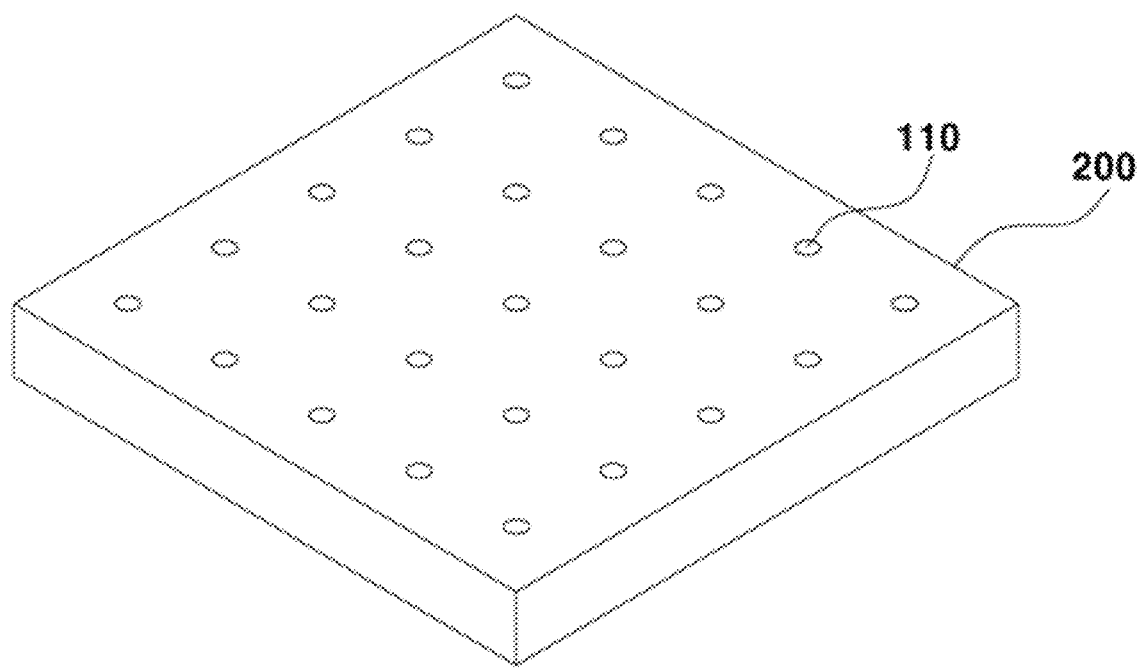
FIGS. 16A, 16B, and 17 are views illustrating a method of forming a base layer according to various embodiments.
Figure 16B:
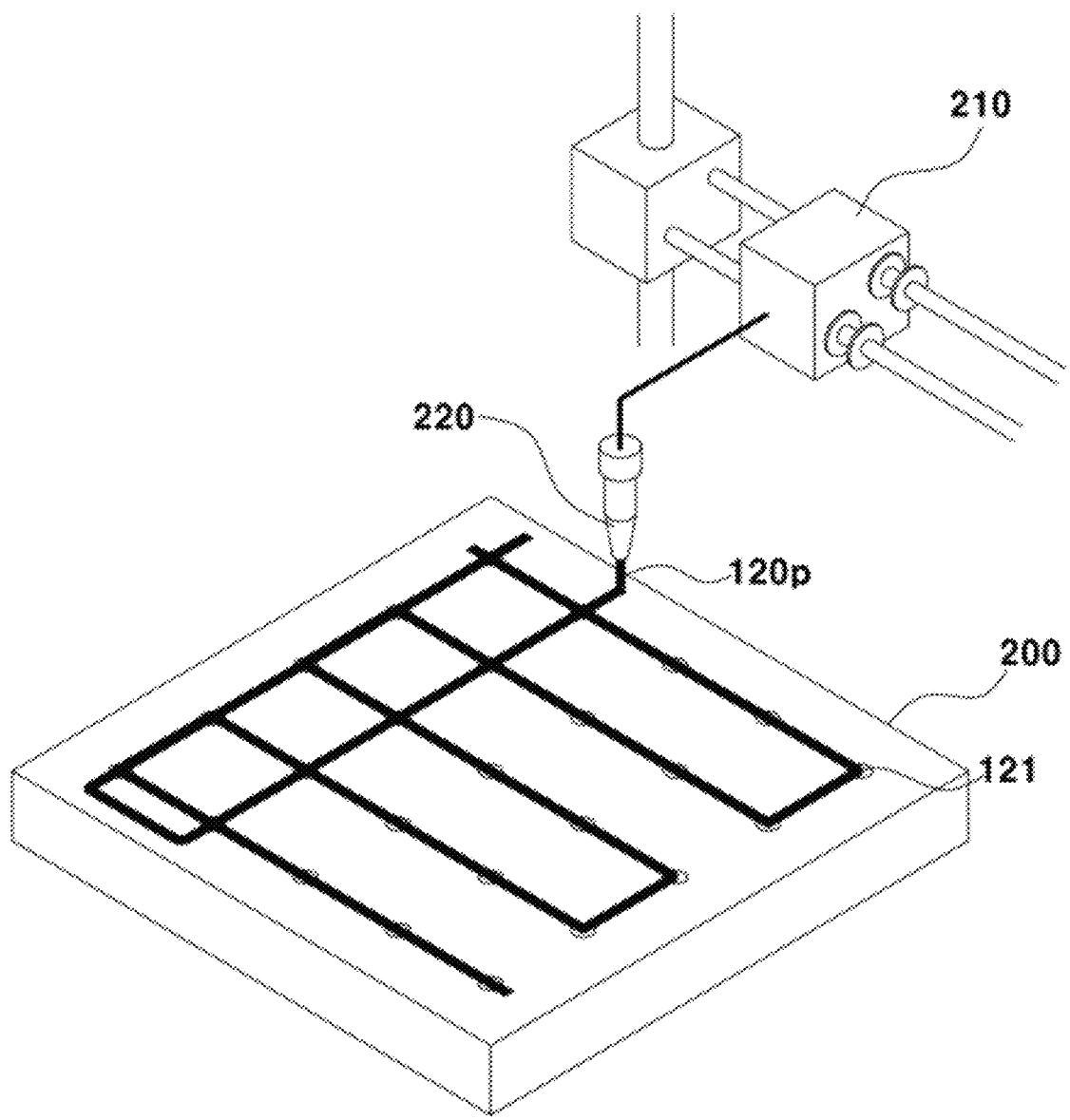
Figure 17:
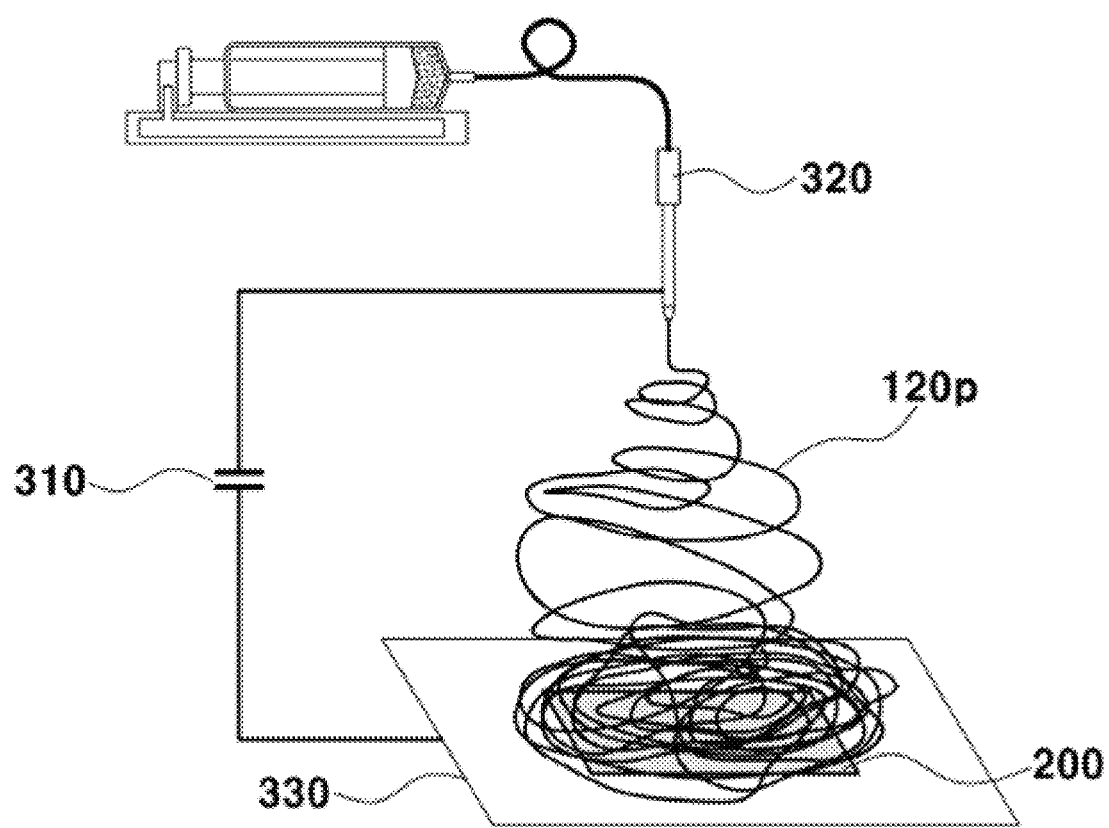

FIGS. 16A, 16B, and 17 are views illustrating a method of forming the base layer 120 according to various embodiments.

Referring to FIG. 16A, constituent materials for forming the microneedles 110 are injected into a plurality of cavities of the mold 200. The plurality of cavities each have an negative shape for forming the microneedle 110. Then, referring to FIG. 16B, forming the base layer (S200) is performed by a printing method in which at least one or more nozzles 220 configured to eject a precursor 120p of the base layer 120 are moved on the plurality of microneedles 110 to form the linear portions 121 configured to connect the microneedles 110 neighboring each other. A 3D printer 210 may be used to form the base layer 120, and various known technologies relating to 3D printing may be used. According to an embodiment of the present invention, since the base layer 120 may be formed in any size and shape using 3D printing technology, the microneedle patch 100 may be fabricated to be easily attached to various target sites such as under an eye, around the mouth, an arm, a shoulder, and the abdomen.

Referring to FIG. 17, in an embodiment, the forming of the base layer (S200) may be performed by an electrospinning method in which the precursor 120p of the base layer 120 is ejected using an electric field to form the linear portions 121 configured to connect the microneedles 110 neighboring each other. A high voltage may be applied between a nozzle 320 configured to eject the precursor 120p of the base layer 120 and a collecting plate 330 configured to collect the linear portions 121 formed from the precursor 120p of the base layer 120. The high voltage may be applied by a voltage supply source 310. When the high voltage is applied, due to a mutual electrostatic repulsive force between surface charges and/or the Coulomb force applied to an external electric field, droplets of the precursor 120p of the base layer 120 may elongate in the shape of a conical funnel (the shape of a Taylor cone), spinning of the precursor 120p of the base layer 120 may occur from the funnel shape, and the linear portions 11 may be formed on the collecting plate 330. In an embodiment, the base layer 120 formed on the collecting plate 330 may be separated and joined to the microneedles 110, or the collecting plate 330 may include the mold 200 in which the microneedles 110 are formed, and thus without separating and moving the formed base layer 120, the linear portions 121 may be formed on the collecting plate 330 to form the microneedle patch 100.

In another embodiment, the step S200 of forming the base layer 120 may be performed by laser cutting. When a pre-processing sheet is fabricated using materials for constituting the base layer 120, and the pre-processing sheet is irradiated with a laser beam, the laser beam may heat a material constituting the sheet so that the material melts or evaporates. The above-given details may be referenced for the materials constituting the base layer 120. For the laser cutting, a processing gas may be supplied to remove dust or residue generated during the laser cutting, wash off a surface of the sheet so that the sheet is not contaminated, or manage chemical interactions. According to an embodiment of the present invention, the materials constituting the base layer 120 are not limited to specific materials, the base layer 120 including various kinds of materials may be easily formed, a pattern may be formed with high accuracy, and since equipment used for the laser cutting does not wear out, there are advantages in that cost for maintenance and repair of the equipment may be reduced and the equipment may be used for a long period of time.

In still another embodiment, the step S200 of forming the base layer 120 may be performed by molding. The precursor 120p of the base layer may be provided to an positive or negative mold of a predetermined pattern that is for forming the pattern, the precursor 120p may be heat-treated or dried to form the base layer 120, and then the base layer 120 may be separated from the mold. The mold may be, but is not limited to, a silicone mold or a polymer mold. The heat treatment for forming the base layer 120 may be replaced by providing light or electron beams in the case in which the precursor 120p of the base layer is a photocurable material or an electron beam curable material. These are non-limiting examples, and various other known molding technologies may be used.

Third Embodiment

Figure 18A:
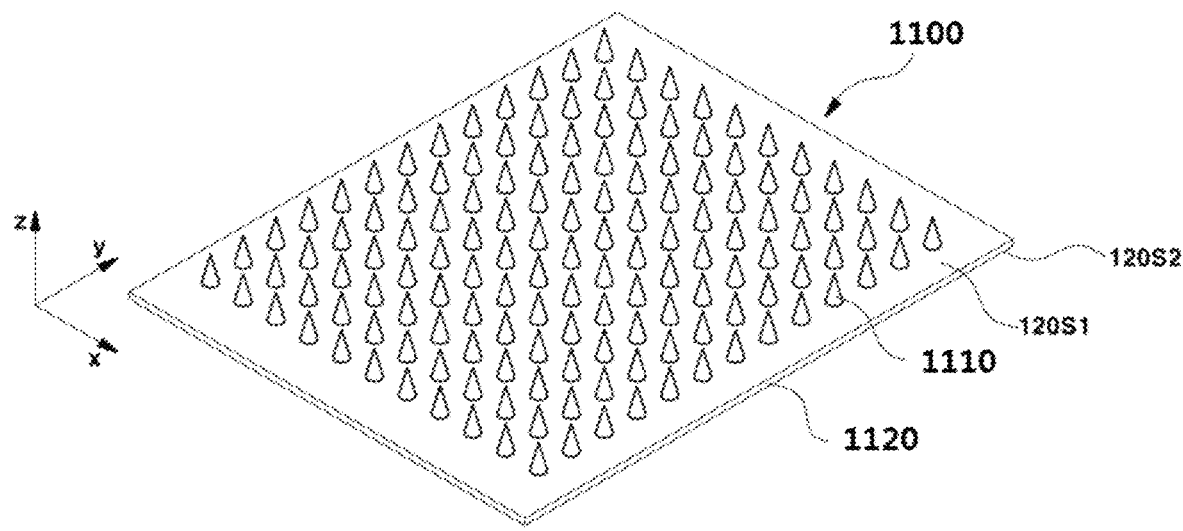
FIG. 18A is a view illustrating a microneedle patch according to an embodiment of the present invention.
Figure 18B:
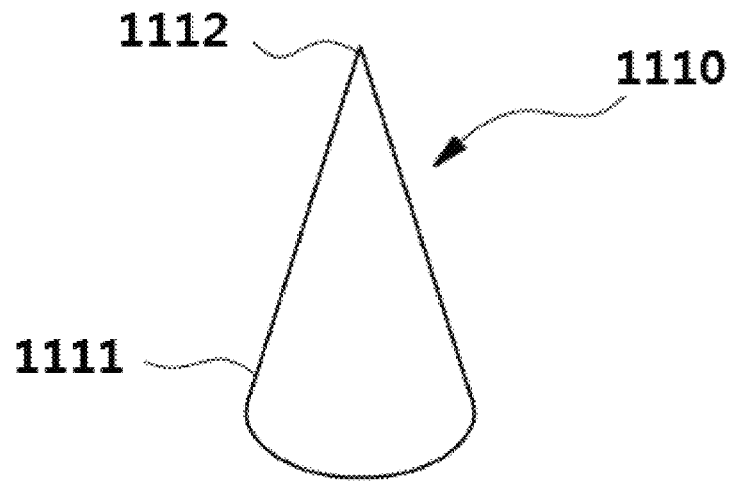
FIG. 18B is a view illustrating a microneedle according to an embodiment of the present invention.

FIG. 18A is a perspective view illustrating a microneedle patch 1100 according to an embodiment of the present invention, and FIG. 18B is a view illustrating a microneedle 1110 according to an embodiment of the present invention.

Referring to FIG. 18A, in an embodiment, the microneedle patch 1100 may include a plurality of microneedles 1110 and a water-soluble base layer 1120 configured to support the plurality of microneedles 1110. The microneedles 1110 may be arranged on the water-soluble base layer 1120 that expands in the first direction x and the second direction y and may be spaced a predetermined distance apart and arranged in the first direction x and/or the second direction y to form a microneedle array. In an embodiment, the predetermined distance may be in a range of 100 μm to 10 mm. The water-soluble base layer 1120 may be formed in the shape of a plate having both surfaces 120S1 and 120S2, and the plurality of microneedles 1110 may be two-dimensionally arranged in a third direction z on a first surface 120S1 of the both surfaces 120S1 and 120S2. The term "two-dimensionally arranged" may refer to the plurality of microneedles 1110 being arranged to form a plane on any one of the first surface 120S1 of the water-soluble base layer 1120 or a second surface 120S2, which is a surface opposite the first surface 120S1. In this case, the plurality of microneedles 1110 may form a microneedle layer on the water-soluble base layer 1120.

Referring to FIG. 18B, in an embodiment, the microneedle 1110 may have an upper end portion 1112 and a base portion 1111. The base portion 1111 of the microneedle 1110 is a portion joined to the base layer 1120, and the upper end portion 1112 is a fore-end when the microneedle is inserted into a living body surface. In an embodiment, a diameter of the microneedle 1110 may decrease in a direction from the base portion 1111 to the upper end portion 1112. For example, as illustrated in FIG. 18B, the microneedle 1110 may have a conical shape, the upper end portion 1112 may be a sharp end portion, and a bottom surface of the base portion 1111 may be a flat surface portion. A cross-section of the base portion 1111-side end portion of the microneedle 1110 is not limited to having a circular shape and may also have a polygonal shape such as a triangular shape, a quadrangular shape, or a pentagonal shape, or a combination thereof. In another embodiment, in the microneedle 1110, a portion at the base portion 1111-side may be formed in the shape of a pillar with a constant diameter, and a portion at the upper end portion 1112-side may have a conical shape, a polygonal pyramid shape such as a triangular pyramid shape or a quadrangular pyramid shape, or a combination thereof extending from the shape of the pillar. In still another embodiment, the microneedle may have the shape of a pillar with a constant diameter from the base portion 1111 to the upper end portion 1112. In an embodiment of the present invention, in the case in which the upper end portion 1112 includes a sharp end portion, when attaching the microneedle patch 1100 to a target site, the sharp end portion may allow the microneedle 1110 to be easily inserted into a living body surface, and as will be described below, pharmaceutically, medically, or cosmetically effective materials contained in at least a partial region of the microneedle 1110 may easily enter the dermis or body through a channel in the living body skin that is formed due to the insertion of the microneedles 1110. Thus, it is possible to provide the microneedle patch 1100 that may efficiently deliver the effective materials.

In an embodiment, the plurality of microneedles 1110 may include a biodegradable material. The biodegradable material may be a monosaccharide, a polysaccharide, a biodegradable hydrogel, a biodegradable polymer, or a combination thereof. For example, the biodegradable material may be: a bio-derived soluble material that is at least any one of chitosan, collagen, gelatin, HA, alginic acid, pectin, carrageenan, chondroitin (sulfate), dextran (sulfate), polylysine, carboxymethyl titine, fibrin, agarose, pullulan, and cellulose; a biocompatible material that is at least any one of PVP, PEG, PVA, HPC, HEC, HPMC, sodium carboxymethyl cellulose, polyalcohol, gum arabic, alginate, cyclodextrin, dextrin, glucose, fructose, starch, trehalose, glucose, maltose, lactose, lactulose, fructose, turanose, melitose, melezitose, dextran, sorbitol, xylitol, pallatinite, polylactic acid, polyglycolic acid, polyethylene oxide, polyacrylic acid, polyacrylamide, polymethacrylic acid, and polymaleic acid; a derivative of any of the above-listed materials; or a mixture thereof. The above-listed materials are non-limiting examples, and the embodiment of the present invention is not limited thereto. All kinds of materials that are harmless to the living body and can naturally degrade in the living body may be applied. According to an embodiment of the present invention, since the materials constituting the plurality of microneedles 1110 are biodegradable, there is an advantage in that there is no need to take the microneedles 1110 out from the body after use.

In another embodiment, the plurality of microneedles 1110 may be formed of HA. The HA is a biosynthetic material that is present in a large amount in a living body and is used in cosmetic products or sheet masks due to having a moisturizing effect when applied to the skin. According to an embodiment of the present invention, since the plurality of microneedles 1110 themselves are formed of HA, even when other effective materials are not added into the microneedles 1110, the microneedles 1110 may induce a moisturizing effect when inserted into skin tissue, and it is possible to obtain a significant moisturizing effect and/or a cosmetic effect due to the moisturizing effect even without a device such as an injection needle that causes pain.

In another embodiment, the plurality of microneedles 1110 may be formed of a water-soluble material, and a speed at which the plurality of microneedles 1110 degrade due to moisture may be lower than a speed at which the water-soluble base layer 1120 degrades due to moisture. Accordingly, the plurality of microneedles 1110 may be inserted into the skin first to release effective materials, or, without degrading, the water-soluble base layer 1120 may fix and support the plurality of microneedles 1110 to allow the plurality of microneedles 1110 to degrade and have a predetermined effect, and then the water-soluble base layer 1120 may degrade.

In still another embodiment, the base portion 1111 of the microneedle 1110 may be formed of a water-soluble material, and the upper end portion 1112 of the microneedle 1110 may contain effective materials. In this case, the base portion 1111 may be dissolved and the microneedle 1110 may be easily separated from the water-soluble base portion 1111, and materials of which the upper end portion 1112 may be formed are not limited to materials that may be separated from the water-soluble base layer 1120, and the upper end portion 1112 may be formed of various effective materials which are the same as or different from the material constituting the base portion 1111. Thus, it is possible to provide the microneedle patch 1100 that is multifunctional.

In an embodiment, pharmaceutically, medically, or cosmetically effective materials may be dissolved or dispersed in the plurality of microneedles 1110 or be coated on the plurality of microneedles 1110. For example, the effective materials may be, but are not limited to, proteins, peptides, genes, antibodies, anesthetics, insulin, vaccines, polysaccharides, synthetic organic compounds, synthetic inorganic compounds, or cosmetic components such as skin lightening agents, fillers, wrinkle reducing agents, or antioxidants. The effective materials may be particles which are dispersed in a solvent forming the microneedles 1110, are evenly dissolved in the solvent, or are coated on the microneedles 1110. These are non-limiting examples and do not limit the present invention. The effective materials may be included in the plurality of microneedles 1110 using various other methods.

In another embodiment, the plurality of microneedles 1110 may be coated with a keratolytic agent. The keratolytic agent may include glycolic acid, lactic acid, malic acid, citric acid, tartaric acid, salicylic acid, gluconic acid, galactose, or a combination thereof. The keratolytic agents may be combined in various ways according to water-oil ratio of the skin, and various known arts may be referenced. According to an embodiment of the present invention, since the keratolytic agent breaks up the hard stratum corneum layer which is the outermost layer of the skin, it is possible to prevent the microneedles 1110 from being damaged due to colliding with the stratum corneum layer in the process of being inserted into the skin.

Referring back to FIG. 18A, when moisture is supplied, the water-soluble base layer 1120 of the microneedle patch 1100 may degrade due to the moisture and be removed, and the plurality of microneedles 1110 supported by the water-soluble base layer 1120 may be individualized. In an embodiment, the water-soluble base layer 1120 may be formed of a water-soluble material that is degraded or dissolved due to absorbing moisture. The water-soluble material may include agar, gelatin, carrageenan, PVA, PVP, polyacrylic acid, polyacrylate, or a combination thereof. These are non-limiting examples, and various other kinds of water-soluble materials may be applied. In the case in which the microneedles 1110 are formed of a water-soluble material, the water-soluble base layer 1120 may be formed of a water-soluble material that is the same as or different from the water-soluble material of the microneedles 1110. Preferably, the water-soluble material of the water-soluble base layer 1120 is different from the water-soluble material of the microneedles 1110. In this case, a speed at which the water-soluble base layer 1120 is degraded or dissolved due to moisture may be higher than a speed at which the microneedles 1110 are degraded or dissolved due to moisture.

Figure 19:
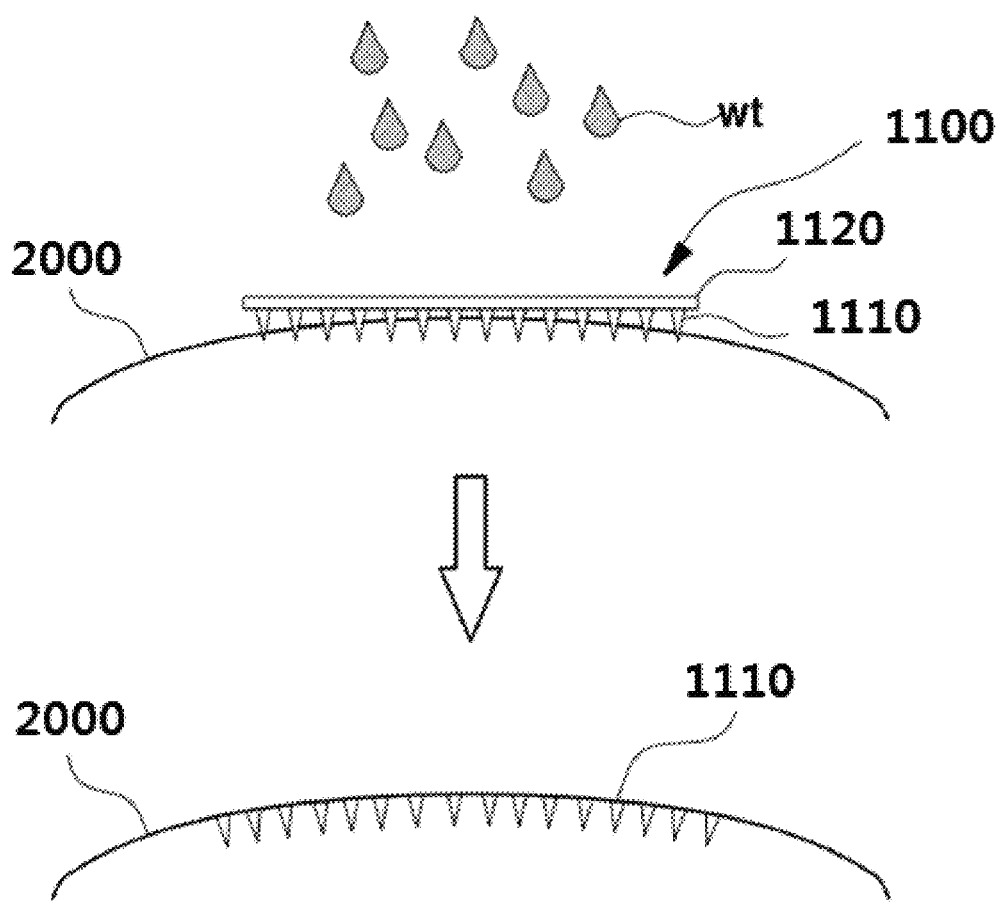
FIG. 19 is a view illustrating how the microneedle patch acts according to an embodiment of the present invention.

FIG. 19 is a view illustrating how the microneedle patch 1100 acts according to an embodiment of the present invention.

Referring to FIG. 19, in an embodiment, during application of the microneedle patch 1100 to the skin, when moisture wt is supplied to the water-soluble base layer 1120 and the water-soluble base layer 1120 degrades due to the moisture wt, causing the water-soluble base layer 1120 to be removed, the plurality of microneedles 1110 which are two-dimensionally arranged may be individualized from each other. The drawing above the arrow shows, as an example, a state immediately after the microneedle patch 1100 is attached to a living body surface such as skin 2000, and the drawing below the arrow shows a state in which the microneedles 1110, which are individualized after the moisture wt is supplied to the microneedle patch 1100 and the water-soluble base layer 1120 degrades and is removed, are each inserted into the skin 2000.

In an embodiment, the microneedles 1110 may remain inserted into the epidermis of the skin 2000 or into an upper portion of the dermis through the epidermis for a predetermined time and then biodegrade or may be weakened due to the moisture wt for dissolving or degrading the water-soluble base layer 1120 and then degrade. After being inserted, the microneedles 1110 may release effective materials included in the microneedles 1110 for the predetermined time.

In an embodiment, for the supply of the moisture wt, after the microneedle patch 1100 is attached to the skin 2000, a moisture supply member may be additionally applied on the microneedle patch 1100 so that the water-soluble base layer 1120 may degrade and be removed. Details relating to a microneedle system 1000 of FIG. 21, which will be given below, may be referenced for detailed description of the moisture supply member. In another embodiment, after the microneedle patch 1100 is attached to the skin 2000, the moisture wt may be provided by washing the skin 2000 or using tools such as a spray. In order to avoid repeated description, the detailed description of the moisture supply member will be given below. According to an embodiment of the present invention, since the process of removing the microneedle patch 1100 after use is omitted, it is possible to obtain a significant cosmetic effect within a short time. Also, since the water-soluble base layer 1120 is removed during use of the microneedle patch 1100, it is possible to prevent a problem of detachment of the microneedle patch 1100 from a living body surface due to movement of the base layer itself that is caused by a curved living body surface or muscle movement in the living body surface, and since the state in which the microneedles 1110 are inserted into the living body surface is stably maintained, the microneedles 1110 may effectively deliver the effective materials. In this way, it is possible to maximize the medical, pharmaceutical, or cosmetic effect of the microneedle patch 1100.

Referring back to FIG. 18A, the first surface 120S1 of the water-soluble base layer 1120, on which the microneedles 1110 are formed, may have adhesiveness. A strength of the adhesiveness is not limited to a specific strength, and the water-soluble base layer 1120 may be defined as having adhesiveness in the case in which, after the water-soluble base layer 1120 comes in contact with a contact surface such as the skin 2000, the water-soluble base layer 1120 remains adhered thereto without being detached. According to an embodiment of the present invention, since, after the microneedle patch 1100 is attached to the skin 2000, the microneedle patch 1100 may remain attached even when without being fixed additionally, it is possible to prevent the microneedle patch 1100 from being easily detached from the skin 2000 before the supply of the moisture wt. Therefore, during use of the microneedle patch 1100, other activities are possible while the microneedle patch 1100 is attached, and there is an advantage in that convenience of use is improved.

Figure 20A:
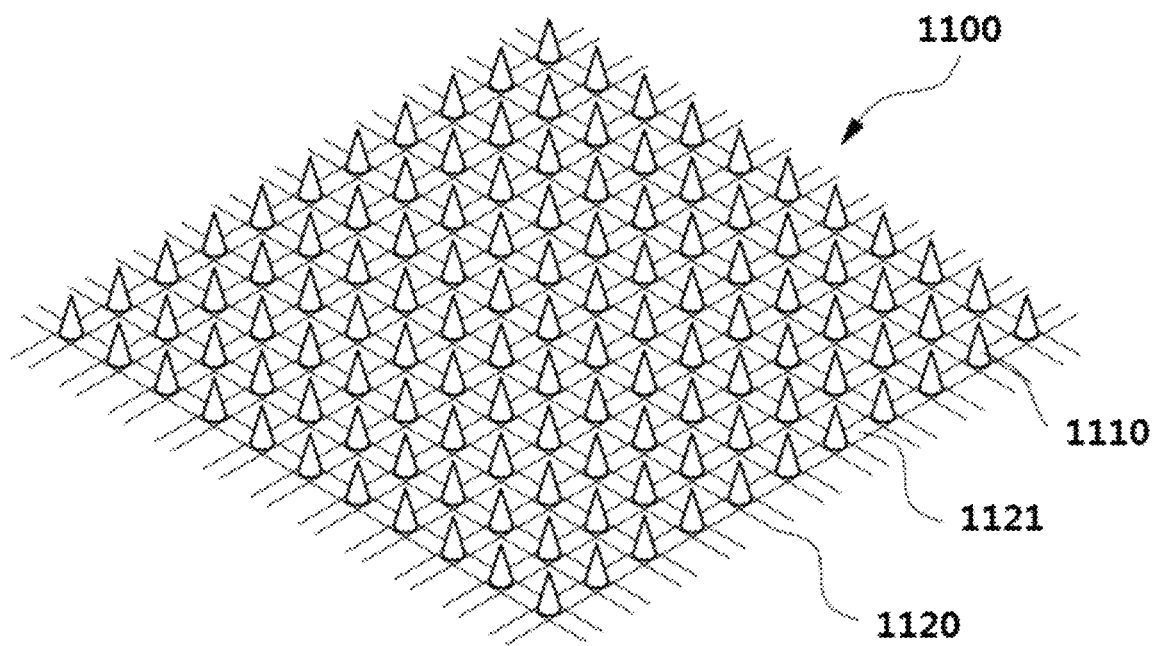
FIGS. 20A to 20C are views illustrating a microneedle patch according to various embodiments of the present invention.
Figure 20B:
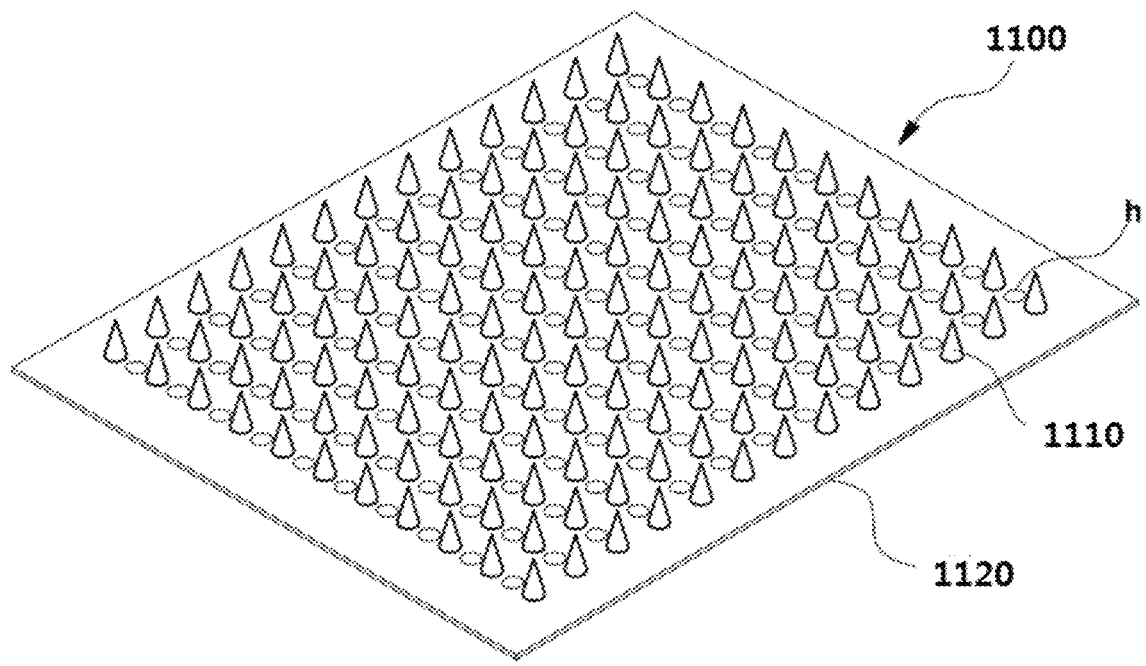
Figure 20C:
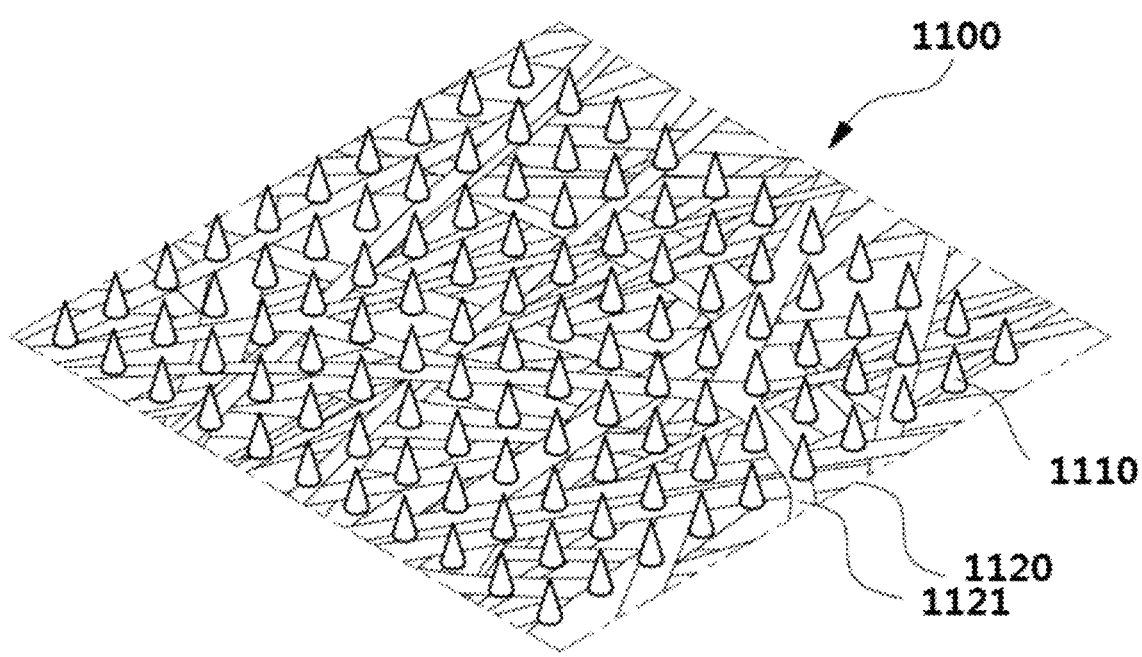

FIGS. 20A to 20C are views illustrating the microneedle patch 1100 according to various embodiments of the present invention.

Referring to FIG. 20A, in an embodiment, the water-soluble base layer 1120 may be a mesh structure including linear portions 1121 that pass the base portions 1111 of the microneedles 1110 neighboring each other among the plurality of microneedles 1110 and are joined to the base portions 1111. The linear portions 1121 may at least partially intersect each other to form the base layer 1120 having a planar structure. In an embodiment, the linear portions 1121 may be a fibrous structure formed by processing a precursor of the base layer 1120. For example, at least some of the linear portions 1121 may have a linear shape while the remaining linear portions 1121 have a curved shape having a predetermined curvature, or the shape of the linear portions 1121 may be a combination of linear shapes in which at least one or more bent portions are present.

Referring to FIG. 20B, in an embodiment, the water-soluble base layer 1120 may be a through-hole structure. For example, the water-soluble base layer 1120 may include a plurality of through-pores h, and the plurality of through-pores h may serve as movement paths along which materials included in a moisture supply member 1200 (see FIG. 21), which is configured to supply moisture to the microneedle patch 1100, move into the skin. The plurality of through-pores h may have a circular shape, a polygonal shape such as a triangular shape or a quadrangular shape, or an elliptical shape.

In another embodiment, the through-pores h may have a slit-shaped linear pattern, a meander pattern, a wavy pattern, or a composite pattern in which linear structures or the above-listed patterns intersect each other. In the case in which the water-soluble base layer 1120 has flexibility or elasticity and is deformed, the size or shape of the through-pores h may change. The area occupied by the plurality of through-pores h relative to the entire area of the water-soluble base layer 1120 may be in a range of 10% to 80%. The elasticity or flexibility of the water-soluble base layer 1120 may be improved with an increase in the area occupied by the plurality of through-pores h. According to an embodiment of the present invention, since the plurality of through-pores h are formed in the water-soluble base layer 1120, as compared to the case in which the plurality of through-pores h are not present, the volume or area occupied by solids relative to the entire area of the water-soluble base layer 1120 is smaller, and the amount of moisture absorbed by the water-soluble base layer 1120 which is formed of a water-soluble material is smaller. Therefore, it is possible to minimize a side effect in which the water-soluble base layer 1120 absorbs moisture from the skin rather than providing moisture thereto.

Referring to FIG. 20C, in an embodiment, the water-soluble base layer 1120 may have a nonwoven structure. Instead of intersecting each other and being fixed to form a woven fabric, the plurality of linear portions 1121 constituting the water-soluble base layer 1120 may be randomly arranged and form a nonwoven structure. According to an embodiment of the present invention, since the linear portions 1121 may be randomly arranged, a speed of producing the water-soluble base layer 1120 may be improved, and production yield of the microneedle patch 1100 may be increased.

Figure 21:
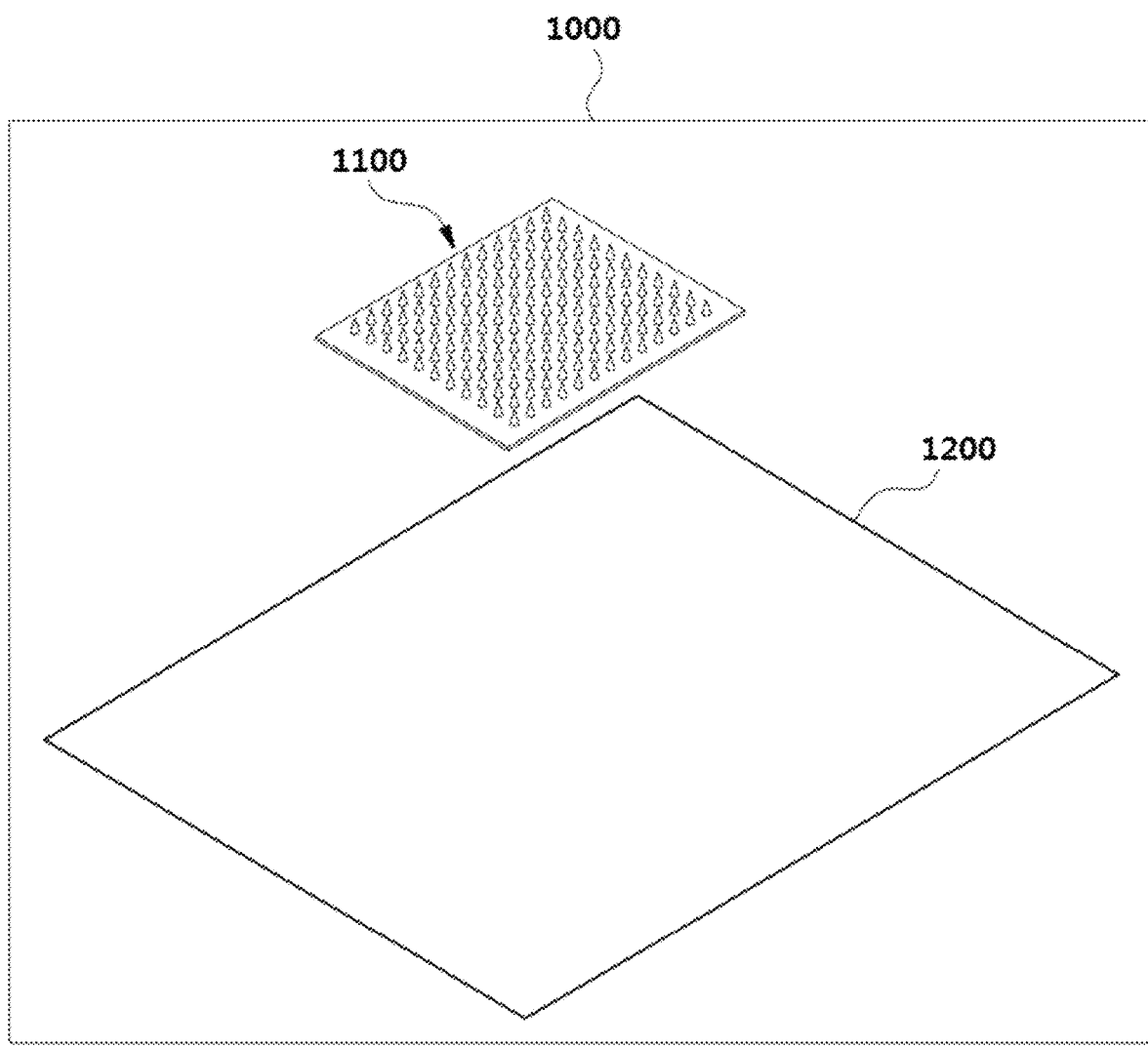
FIG. 21 is a view illustrating a microneedle system according to an embodiment of the present invention.

FIG. 21 is a view illustrating the microneedle system 1000 according to an embodiment of the present invention.

Referring to FIG. 21, in an embodiment, the microneedle system 1000 may include the plurality of microneedles 1110 each having the upper end portion 1112 and the base portion 1111 and which are individualized from each other, the water-soluble base layer 1120 joined to the plurality of microneedles 1110 to allow the plurality of microneedles 1110 to be two-dimensionally arranged, and the moisture supply member 1200 configured to supply moisture to the water-soluble base layer 1120 and remove the water-soluble base layer 1120 so that the plurality of microneedles 1110, which are two-dimensionally arranged, are individualized. For detailed description of the plurality of microneedles 1110 and the water-soluble base layer 1120, the details given above with reference to FIG. 18A or 20C may be referenced within the non-contradictory range.

In an embodiment, the moisture supply member 1200 may be a carrier carrying moisture or a material containing a large amount of moisture, such as a moisture-containing sheet, a hydrogel sheet, or a sheet mask. For example, the carrier may be, but is not limited to, nonwoven fabric. The carrier may have any form that can hold and discharge moisture. In another embodiment, the moisture supply member 1200 may not include a separate carrier, and a moisturizing gel, a moisturizing cream, a toner, and an essence, or a combination thereof may be directly applied on the microneedle patch 1100.

In still another embodiment, the moisture supply member 1200 may be a natural moisture carrier. The natural moisture carrier may be a natural face mask using natural ingredients such as cucumber, potato, yogurt, or rice water. These examples are non-limiting examples, and any kind of materials containing moisture may be applied.

In an embodiment, the moisture supply member 1200 may include pharmaceutically, medically, or cosmetically effective materials. The moisture supply member 1200 may include the same kind of effective material as the plurality of microneedles 1110 or include a different kind of effective material from the plurality of microneedles 1110. The above-given details relating to the effective materials included in the plurality of microneedles 1110 may be referenced for detailed description of the effective materials. The microneedles 1110 pass through the epidermis layer of the skin or the epidermis layer and an upper portion of the dermis layer and degrade inside the skin, thereby forming a material exchange channel between the skin and the moisture supply member 1200 and allowing the effective materials to easily permeate into the skin. According to an embodiment of the present invention, since the effective materials permeate into the skin through the material exchange channel, it is possible to obtain an efficient effective material delivery effect, unlike in the case in which the effective materials are simply provided to the skin.

In an embodiment, the water-soluble base layer 1120 may include a material that absorbs heat when dissolved. The material may include a compound having a negative heat of dissolution. For example, the material may include ammonium nitrate, sodium chloride, potassium chloride, xylitol, barium hydroxide, barium oxide, potassium magnesium sulfate, aluminium potassium sulfate, sodium borate, sodium phosphate, or a combination thereof. According to an embodiment of the present invention, since the water-soluble base layer 1120 includes materials having a negative heat of dissolution and the materials absorb heat of dissolution as the water-soluble base layer 1120 is dissolved due to moisture, a cooling or refreshing sensation may be provided to the skin, temperature of the skin may be lowered to soothe the skin irritated by hot weather, and there is an effect of suppressing sebum secretion.

In an embodiment, the microneedle system 1000 may be formed of a predetermined package (not illustrated), and the package may include a first accommodating region (not illustrated) configured to accommodate the microneedle patch 1100 and a second accommodating region (not illustrated) configured to accommodate the moisture supply member 1200 and isolated from the first accommodating region. The package may isolate the microneedle patch 1100 and the moisture supply member 1200 to prevent the water-soluble base layer 1120 from absorbing moisture and degrading before use.

In an embodiment, the first accommodating region and/or the second accommodating region may be spaces partitioned by an isolating member inside a single pouch or packaging. For example, the isolating member may be a synthetic resin film. In another embodiment, the first accommodating region may be provided by a first support film member, and the second accommodating region may be provided by a second support film member. The first support film member and/or the second support film member may include an upper support member and a lower support member, and the microneedle patch 1100 and/or the moisture supply member 1200 may be disposed between the upper support member and the lower support member and sealed.

Figure 22:
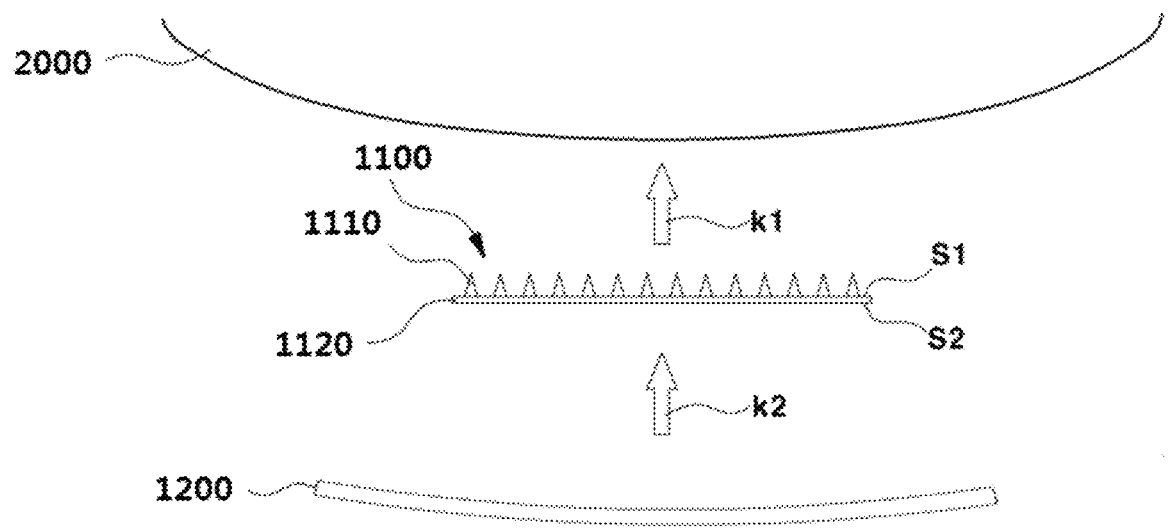
FIG. 22 is a view illustrating a method of applying the microneedle system according to an embodiment.

FIG. 22 is a view illustrating a method of applying the microneedle system 1000 according to an embodiment.

Referring to FIG. 22, in an embodiment, first, the microneedle patch 1100 may be attached to the skin so that a first surface S1 of the water-soluble base layer 1120 that is joined to the microneedles 1110 contact with the skin (k1). Then, after a predetermined amount of time or immediately after the step k1, the moisture supply member 1200 may be placed on a second surface S2 opposite the first surface S1 (k2). In an embodiment, a film for moving the microneedle patch 1100 onto the skin may be provided on the second surface S2 of the microneedle patch 1100, and a user may use the film to attach the first surface S1 of the microneedle patch 1100 to the skin (k1) and then remove the film. This is a non-limiting example, and thus embodiments of the present invention are not limited to the above-described embodiment, and various other known arts may be referenced.

In an embodiment, a predetermined effective material may be provided onto the first surface S1 of the microneedle patch 1100 before the attaching of the microneedle patch 1100 to the skin 2000 (k1), and then the microneedle patch 1100 to which the effective material is provided may be attached to the skin 2000 (k1). Alternatively, the predetermined effective material may be provided onto the skin 2000 before the attaching of the microneedle patch 1100 (k1), and then the microneedle patch 1100 may be attached to the skin 2000 to which the predetermined effective material is provided (k1). According to an embodiment of the present invention, since the predetermined effective material is provided in a region between the skin 2000 and the microneedle patch 1100, when the microneedle patch 1100 is attached, the upper end portion 1112 of the microneedle 1110 may be inserted into the skin 2000 and physically allow the effective material to move into the skin 2000, and the microneedle 1110 may form an effective material movement path. Thus, the effective material may efficiently permeate into the skin 2000, and the effect of the effective material may be maximized. Also, since the effective material is not necessarily provided in the form of being included in the microneedle patch 1100, and lotion, cream, gel, natural face masks that the user uses or ingredients such as vitamins may be applied as the effective material, the microneedle patch 1100 is easy to use, and various effective materials may be applied. Thus, there is an advantage in that the microneedle patch 1100 has a wide usable range.

In an embodiment, a method of fabricating the microneedle system 1000 may include preparing the plurality of microneedles 1110, each having the upper end portion 1112 and the base portion 1111 and which are individualized from each other, forming the base layer 1120 having a planar structure that is formed of a water-soluble material and joined to the plurality of microneedles 1110, and providing the moisture supply member 1200 configured to supply moisture to the base layer 1120.

The present invention described above is not limited to the above-described embodiments and the accompanying drawings, and it should be apparent to those of ordinary skill in the art to which the present invention pertains that various substitutions, modifications, and changes are possible within the scope not departing from the technical idea of the present invention.

DESCRIPTION OF REFERENCE NUMERALS

| | |
|---|---|
| 1: microneedle patch | BU: base layer |
| MN: microneedle array | x: first direction |
| y: second direction | m: midpoint |
| EM: effective material | CL: interlayer connecting portion |
| BU1, BU2: two-dimensional re-entrant honeycomb structures | |
| 100: microneedle path | 110: microneedle |
| 111: base portion | 112: upper end portion |
| 120: base layer | 121: linear portion |
| 122: linear portion intersecting region | 130: effective material |
| 120a: first linear portion | 120b: second linear portion |
| 110': some microneedles | 123: only one linear portion present region |
| 200: mold | 110a: first group of microneedles |
| 110b: second group of microneedles | 20: target site |
| 20a: cheek area | 20b: around-the-mouth area |
| 10: moisture | |
| 100a: microneedle patch not containing effective material | |
| 100b: microneedle patch containing effective material | |
| 120p: precursor | 220: nozzle |
| 210: 3D printer | 330: collecting plate |
| 310: voltage supply source | 1100: microneedle patch |
| 1110: microneedle | 1120: water-soluble base layer |
| 120S1: first surface | 120S2: second surface |
| 1112: upper end portion | 1111: base portion |
| wt: moisture | 2000: skin |
| 1000: microneedle system | 1121: linear portion |
| h: pore | 1200: moisture supply member |
| k1: attach | k2: place |

What is claimed is:

1. A microneedle patch comprising:
a base layer including auxetic materials or a mesh structure having a negative Poisson's ratio such that the base layer expands or enlarges in a direction perpendicular to an axis when a tensile force is applied in an axial direction and contracts or reduces in the direction perpendicular to the axis when a compressive force is applied in the axial direction; and
a microneedle array disposed on the base layer,
wherein the base layer further includes:
a plurality of two-dimensional re-entrant honeycomb structures which are spaced apart and stacked, a plurality of two-dimensional cut missing rib structures which are spaced apart and stacked, or mixed structures formed of a combination of the two-dimensional re-entrant honeycomb structures and the two-dimensional cut missing rib structures which are spaced apart and stacked; and
interlayer connecting portions disposed between the two-dimensional re-entrant honeycomb structures which are spaced apart and stacked, disposed between the two-dimensional cut missing rib structures which are spaced apart and stacked, or disposed between the mixed structures in which the two-dimensional re-entrant honeycomb structures and the two-dimensional cut missing rib structures are spaced apart and stacked.

2. The microneedle patch of claim 1, wherein:
the microneedle array has tensile deformation in a first direction due to a tensile force and tensile deformation in a second direction different from the first direction; and
the microneedle array has compressive deformation in the first direction due to a compressive force and compressive deformation in the second direction different from the first direction.

3. The microneedle patch of claim 1, wherein linear portions connecting a plurality of microneedles included in the microneedle array on the mesh structure or linear portions connecting intersection points of the mesh structure have a zigzag or serpentine shape.

4. The microneedle patch of claim 1, wherein the base layer includes a patterned mesh structure including at least any one of a two-dimensional cut missing rib structure or a two-dimensional re-entrant honeycomb structure.

5. The microneedle patch of claim 1, wherein the plurality of microneedles are fixed to intersection points of the mesh structure.

6. The microneedle patch of claim 1, further comprising a plurality of pharmaceutically, medically, or cosmetically effective materials,
wherein the effective materials are dissolved or dispersed in a plurality of microneedles included in the microneedle array or are coated on surfaces of the plurality of microneedles.

7. The microneedle patch of claim 6, wherein:
a first group of microneedles among the plurality of microneedles includes a first effective material among the plurality of effective materials; and
a second group of microneedles different from the first group includes a second effective material among the plurality of effective materials.

8. The microneedle patch of claim 1, further comprising an adhesive layer disposed between the base layer and a plurality of microneedles included in the microneedle array.

9. A microneedle patch comprising:
a base layer including auxetic materials or a mesh structure having a negative Poisson's ratio; and
a microneedle array disposed on the base layer,
wherein:
the microneedle array includes a plurality of microneedles each having an upper end portion and a lower end portion and which are individualized from each other; and the base layer passes the lower end portions of the microneedles neighboring each other among the plurality of microneedles, is joined to the lower end portions of the microneedles neighboring each other, and is formed of a water-soluble material.

10. A method of fabricating a microneedle patch, the method comprising:
forming a base layer including a mesh structure or auxetic materials having a negative Poisson's ratio such that the base layer expands or enlarges in a direction perpendicular to an axis when a tensile force is applied in an axial direction and contracts or reduces in the direction perpendicular to the axis when a compressive force is applied in the axial direction; and
forming a microneedle array on the base layer;
wherein the base layer further includes:
a plurality of two-dimensional re-entrant honeycomb structures which are spaced apart and stacked, a plurality of two-dimensional cut missing rib structures which are spaced apart and stacked, or mixed structures formed of a combination of the two-dimensional re-entrant honeycomb structures and the two-dimensional cut missing rib structures which are spaced apart and stacked; and
interlayer connecting portions disposed between the two-dimensional re-entrant honeycomb structures which are spaced apart and stacked, disposed between the two-dimensional cut missing rib structures which are spaced apart and stacked, or disposed between the mixed structures in which the two-dimensional re-entrant honeycomb structures and the two-dimensional cut missing rib structures are spaced apart and stacked.

11. The method of claim 10, wherein the forming of the base layer or the forming of the microneedle array is performed by 3D printing, laser cutting, molding, or a combination thereof.

12. The method of claim 11, wherein the 3D printing includes stereolithography (SLA), digital micromirror device-based projecting printing (DMD-PP), two-photon polymerization (2PP), fused deposition modelling (FDM), inkjet, bioprinting, selective laser melting (SLM), electron beam melting (EBM), or a combination thereof.

* * * * *